(12) United States Patent
Sakurai et al.

(10) Patent No.: US 6,492,162 B1
(45) Date of Patent: Dec. 10, 2002

(54) APPARATUS FOR THE RECOVERY OF NUCLEIC ACIDS

(75) Inventors: Toshinari Sakurai, Hitachinaka (JP); Shinichi Fukuzono, Hitachinaka (JP); Kenji Yasuda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/457,290

(22) Filed: Dec. 9, 1999

Related U.S. Application Data

(63) Continuation-in-part of application No. 09/179,188, filed on Oct. 27, 1998.

(30) Foreign Application Priority Data

Dec. 10, 1998 (JP) .............................. 10-351454

(51) Int. Cl.⁷ ............................ C12M 1/00; C12M 3/00; C12N 11/02; C07H 21/00
(52) U.S. Cl. ................... 435/285.1; 435/91.1; 435/177; 435/283.1; 435/289.1; 536/25.4
(58) Field of Search .......................... 536/25.4; 435/87, 435/91.1, 177, 178, 180, 283.1, 285.1, 289.1

(56) References Cited

U.S. PATENT DOCUMENTS

| | | | |
|---|---|---|---|
| 4,935,342 A | 6/1990 | Seligson et al. | 435/6 |
| 5,234,809 A | 8/1993 | Boom et al. | 435/91 |
| 5,556,598 A | 9/1996 | Raybuck et al. | 422/10 D |
| 6,048,457 A | 4/2000 | Kopaciewicz et al. | 210/321.6 |

FOREIGN PATENT DOCUMENTS

| | | |
|---|---|---|
| JP | 63-88456 | 4/1988 |
| JP | 63-117262 | 5/1988 |
| JP | 63-154696 | 6/1988 |
| JP | 2-289596 | 11/1990 |
| JP | 7-250681 | 10/1995 |
| JP | 8-320274 | 12/1996 |

OTHER PUBLICATIONS

Saiki, Randall K. et al, "Primer–Directed Enzymatic Amplification of DNA with Thermostable DNA Polymerase," Science, vol. 239, 1988, pp. 487–491.

Ohshima, Toshio et al, "Usefulness of the Positive Internal Control for Detection of *Mycobacterium tuberculosis* in a Fully Automated PCR Analyzer COBAS AMPLICOA," JJCLA, vol. 22, 1997, pp. 145–150.

Vogelstein, Bert et al, "Preparative and analytical purification of DNA from agarose," Proc. Natl. Acad. Sci. USA, vol. 76, No. 2, pp. 615–619, Feb. 1979, pp. 615–619.

Marko, M.A. et al, "A Procedure for the Large–Scale Isolation of Highly Purified Plasmid DNA Using Alkaline Extraction and Binding to Glass Powder," Anal. Biochem 121, 1982, pp. 382–387.

Chen, Carton W. et al, "Recovery of DNA Segments from Agarose Gels," Anal. Biochem. 101, 1980, pp. 339–341.

Molecular Cloning: a laboratory manual–2nd ed., Cold Spring Harbor Laboratory Press (1989).

Excerpt from Sambrook et al, "Commonly Used Techniques in Molecular Cloning", 2nd Edition, CSH, 1989.

*Primary Examiner*—David M. Naff
(74) *Attorney, Agent, or Firm*—Mattingly, Stanger & Malur, P.C.

(57) ABSTRACT

Methods and apparatus are provided for the recovery of nucleic acids from a nucleic acid-containing material by which nucleic acids can be rapidly and easily recovered at a high purity without deteriorating the yield. The methods are composed of step 1 for promoting the release of nucleic acids from a nucleic acid-containing material, step 2 for mixing the released nucleic acids with an accelerator substance for the binding of nucleic acids to a solid phase, step 3 for bringing the mixture in contact with a solid phase bondable to nucleic acids, step 4 for isolating the solid phase from a liquid, step 5 for washing the solid phase with a solution containing a salt, and a step 6 for eluting the nucleic acids from the solid phase. Accordingly, nucleic acids at a suitable purity for genetic tests or gene analyses can be rapidly and easily recovered without the use of hazardous substances. The apparatus may contain a reactor, at least one pipette, a purified product container, transport mechanisms for the reactor and purified product container, motors to control the pipette and transport mechanisms, a mechanical control unit to control the motors, and a computer that controls the mechanical control unit.

7 Claims, 13 Drawing Sheets

APPARATUS FOR THE RECOVERY OF NUCLEIC ACIDS

CROSS-REFERENCE TO RELATED APPLICATION

This is a continuation-in-part of U.S. Ser. No. 09/179,188 filed on Oct. 27, 1998, the contents of which are incorporated herein by reference.

BACKGROUND OF THE INVENTION

1. Field of the invention

The present invention relates to a method for the recovery of nucleic acids from a nucleic acid-containing substance. In more detail, it relates to a method for the recovery of nucleic acids, which is suitable for an automatic device for the recovery of nucleic acid components as endogenous or exogenous genes from humor components for gene diagnosis by means of nucleic acid assays, or suitable for an automatic device for the recovery of plasmid DNAs from recombinant *E. coli* or the like for base sequencing of nucleic acids.

2. Description of the Related Art

A multitude of genetic technologies have been developed based upon advances in molecular biology, and a number of morbid genes have been isolated and identified according to these technologies. As a result, molecular biological techniques have been adopted as techniques for diagnosis or examination in the field of medical care so as to enable diagnosis which have been unable to conduct or to shorten the period of examination remarkably.

The significant advances largely owe to gene amplification techniques, in particular to polymerase chain reaction (hereinafter referred to as PCR: Saiki et al., Science, 239, 487–491(1988)) techniques.

The PCR technique enables nucleic acids in a solution to amplify sequence-specifically so that it provides, for example, an indirect proof of the presence of a trace quantity of a virus in serum by amplifying and detecting nucleic acids as the viral gene.

The PCR technique is, however, somewhat disadvantageous in the use for clinical daily examinations. In particular, there are some difficulties in extraction and purification steps of nucleic acids in a pretreatment according to this technique, whereas the extraction and purification steps of nucleic acids have been indicated to be key steps (Ooshima et al., JJCLA 22(2),145–150(1997)).

These difficulties are attributed to inhibitory factors remaining in the purification step of nucleic acids, and known inhibitory factors include hemoglobin in blood, surfactant used in the extraction step and the like.

In addition, the extraction step requires a complicated procedure and a large amount of skilled labor. Therefore, this step is an obstacle to a new introduction of the genetic test into laboratories of hospitals, and the automatization of this step has been demanded.

On the contrary, plasmid DNAs are frequently used as materials for genetic engineering, and automatization of the extraction and purification steps of nucleic acids has been demanded from the viewpoint of labor savings in institutions for molecular biological research, as well as in the laboratories.

SUMMARY OF THE INVENTION

As a method for the recovery of nucleic acids from a biological sample at a high purity and being free from inhibitory factors, there has been known a method for the recovery of nucleic acids comprising the steps of allowing a surfactant to act on a biological sample in the presence of a protease to release nucleic acids, mixing the released nucleic acids with phenol (and chloroform), repeating aqueous phase (water phase)-organic phase isolation by a centrifuge several times and then recovering the nucleic acids as sediments from the aqueous phase with the use of an alcohol.

This method, however, has some disadvantages due to the use of an organic solvent such as phenol, a toxic substance, in the steps. To be more specific, an organic solvent such as phenol has the possibilities of dissolving plastics of a device used for the recovery of nucleic acids and of deteriorating the device.

Further, the method noted here requires for a centrifugation step to be effected. This leaves the problem that automation is made extremely difficult to achieve in putting and taking containers into and out of the rotators of a centrifuge and also in fractionating the resultant centrifuged solutions.

In addition, the use of an organic solvent such as phenol requires complicated treatments for discarding the organic solvent.

As other method for the recovery of nucleic acids than the method utilizing the aqueous phase-organic phase isolation, there have been reported a method for the recovery of DNAs from agarose gel utilizing the bonding properties of nucleic acids to the surface of glass in the presence of a chaotropic agent (B. Vogelstein and D. Gillespie, Proc. Natl. Acad. Sci. USA, 76(2),615–619(1979)), or a method for recovering plasmid DNAs from *E. coli* (M. A. Marko, R. Chipperfield and H. C. Birnboim, Anal. Biochem, 121,382–387(1982)).

A method for the recovery of nucleic acids from a biological sample by means of a simpler procedure is described in Japanese Unexamined Patent Publication No. 2-289596. According to this method, nucleic acids can be rapidly recovered by mixing a biological sample with a sufficient amount of a chaotropic agent (such as guanidinium salt) and silica beads and binding the free nucleic acids to a solid phase.

To obtain purified nucleic acids, however, this method requires a procedure for removing the guanidinium salt from the solid phase while retaining the nucleic acids bound to the solid phase, whereas a suitable removing procedure is not described.

For an efficient washing procedure of a solid phase at room temperature, the use of ethanol at least in a 75% concentration has been recommended in the past (C. W. Chen and C. A. Thomas, Jr., Anal. Biochem., 101,339–342 (1980)). As ethanol is a volatile component, the mechanization of the method requires a close-open mechanism of a lid or a cooling mechanism for preventing ethanol from evaporation, and this invites upsizing of the device or deterioration of its reliability.

In addition, the method requires a washing step with 70% ethanol and/or acetone and hence requires a removing procedure of acetone by drying. When ethanol at a concentration of 70% or more and/or acetone, both of which are volatile, is mounted on an automatic device, the device requires a highly airtight chamber and a close-open mechanism of a lid and/or a cooling mechanism for preventing volatilization of the reagents, as described above.

The use of acetone has possibilities of dissolving plastics of a device employed for the recovery of nucleic acids and deteriorating the device due to its strong properties as an organic solvent, as mentioned above.

Therefore, materials of the device, cases and dispensers or other utensils to be used are remarkably limited. In addition, as acetone has acute toxicity and is inflammable, the release of acetone into the environment accompanied with the evaporation procedure should be avoided completely.

Japanese Unexamined Patent Publication No. 63-154696 discloses a method of isolating and purifying nucleic acids from an aqueous solution of a biological sample containing nucleic acids.

According to this method, an objective nucleic acid is recovered in the following manner: Initially, a biological sample is charged to a column filled with an anion exchanger, and the column is washed with an aqueous solution of sodium chloride to avoid the elution of an objective nucleic acid and to cleanse nonbinding components inclusive of carboxylated mucopolysaccharides. The objective nucleic acid is then recovered by eluting from the column with an aqueous solution of sodium chloride at such a concentration as to elute the objective nucleic acid.

The method just mentioned above ensures the recovery of an objective nucleic acid without using harmful substances.

This method where a sodium chloride aqueous solution is used as a washing solution, however, provides only a low recovery of nucleic acids. Accordingly, demands have been made to provide a method for recovering nucleic acids at a higher recovery yield.

To overcome the use of organic solvents in fractionating a nucleic acid, a method for the separation of nucleic acids is known in which a water-insoluble hybrid-forming carrier is supported on the surfaces of non-porous particles of 0.01–50 pm in particle diameter, the carrier having a single-chain nucleic acid bonded at least partly thereto (Japanese Unexamined Patent Publication No. 63-117262).

In the method disclosed by this publication, the carrier capable of hybridization with a nucleic acid is brought into contact with a nucleic acid-containing solution so that the hybridized carrier can be separated from that solution with no need for organic solvents. Separation of the carrier from the solution, however, needs a centrifugation step with eventual difficulty in attaining automation.

A method for the recovery of nucleic acids is also known in which cellulose or the like is fixed to have nucleic acid sequence that is partially compensatory for base sequence of an objective nucleic acid, followed by column-chromatographic recovery of the objective nucleic acid (Molecular Cloning: a laboratory manual—2nd Ed., Cold Spring Harbor Laboratory Press (1989)).

In such instance, however, the use of column chromatography has the drawback that it causes poor efficiency when utilizing gravity drop, entailing large-scale apparatus since the system needs arrangement of pumps and the like.

Alternatively, as another conventional means evolved to omit a separation step, there may be applied a separating technique of B/F (bond form/free form) in which an antigen-antibody reaction is utilized with the use of an immunity analysis apparatus.

This technique is suitably useful for the case where probe chips are used, as a sample, which are provided with shoulders and with a resin having an antibody bonded physically or chemically thereto and filled between the shoulders (Japanese Unexamined Patent Publication No. 63-88456). Such conventional art, though excellent, is defective in that the probe chip sample is extremely difficult to form because it is necessary to encapsulate the resin between the shoulders.

A method for the recovery of nucleic acids without use of organic solvents is further known in which a nucleic acid is recovered by subjecting of the latter to non-specific bonding to silica in the presence of a chaotropic agent. However, this method fails to recover a nucleic acid by means of specific sequencing.

It is, therefore, an object of the present invention to provide a method and apparatus for the recovery of nucleic acids from a material containing nucleic acids, by which nucleic acids can be recovered rapidly and easily at a high recovery and high purity without deteriorating the yield.

It is another object of the invention to provide a method for the recovery of nucleic acids, which is suitable for apparatus for the automatic recovery of nucleic acids from a biological sample at a high recovery yield.

A further object of the invention is to provide a method for the recovery of nucleic acids, which is suitable for apparatus for the automatic recovery of plasmid DNAs from *E. coli* at a high recovery.

Still another object of the invention is to provide a method for and an apparatus for the recovery of nucleic acids which are speedy, simple and inexpensive to recover a highly pure nucleic acid from nucleic acid-containing materials and which are capable of automatically recovering nucleic acid components of specific sequences present in biological samples.

To achieve the above objects, the present invention provides the following constructions.

(1) The invention provides, in a first aspect, a method for the recovery of nucleic acids comprising a step 2 for mixing an accelerator substance for the binding of nucleic acids to a solid phase with a nucleic acid-containing material, a step 3 for making the mixture obtained in step 2 in contact with a solid phase bondable to nucleic acids to form a nucleic acid-binding solid phase, a step 4 for isolating the nucleic acid-binding solid phase from a liquid, a step 5 for washing the nucleic acid-binding solid phase with a solution containing an acetate, and a step 6 for eluting the nucleic acids from the solid phase.

(2) The method may preferably include a step 1 for promoting the release of nucleic acids from the nucleic acid-containing material before the step 2 in the above aspect.

(3) Step 5 in the above method may preferably be composed of a step 5a for removing non-nucleic-acid components from the nucleic acid-binding solid phase by washing, and a step 5b for removing the accelerator substance from the solid phase by washing.

(4) The substance for removing non-nucleic-acid components from the solid phase in step 5a may advantageously be guanidine hydrochloride.

(5) The acetate solution in the first aspect may preferably be a solution containing 0.5 mol/liter or more of potassium acetate.

(6) In a second aspect the invention provides a method for the recovery of nucleic acids from a material containing nucleic acids, which includes a step 2 for mixing an accelerator substance for the binding of nucleic acids to a solid phase with a nucleic acid-containing material, a step 3 for making the mixture obtained in the step 2 in contact with a solid phase bondable to nucleic acids to form a nucleic acid-binding solid phase, a step 4 for isolating the nucleic acid-binding solid phase from a liquid, a step 5 for washing the nucleic acid-binding solid phase with a solution containing 0.2 mol/liter or more of potassium chloride, and a step 6 for eluting the nucleic acids from the solid phase.

(7) The invention in a third aspect provides a method for the recovery of nucleic acids from a material containing nucleic acids, which is composed of a step 2 for mixing an accelerator substance for the binding of nucleic acids to a solid phase with a nucleic acid-containing material, a step 3 for making the mixture obtained in the step 2 in contact with a solid phase bondable to nucleic acids to form a nucleic acid-binding solid phase, a step 4 for isolating the nucleic acid-binding solid phase from a liquid, a step 5 for washing the nucleic acid-binding solid phase with a mixture of an aqueous solution of a salt and an alcohol, and a step 6 for eluting the nucleic acids from the solid phase.

(8) The method described in the third aspect may preferably have a step 7 for removing the alcohol after the elution of nucleic acids from the solid phase in step 6.

(9) The alcohol used in step 5 described in the third aspect may preferably be ethanol at a concentration of less than 50% in the mixture.

(10) The washing solution in step 5 described in the third aspect may advantageously be a solution containing 40% of ethanol and 10 mmol/liter or more of potassium acetate.

(11) The washing solution used in step 5 described in the third aspect may be a solution containing 40% of ethanol and 25 mmol/liter or more of sodium chloride.

(12) The accelerator substance used in step 2 in the above aspects may preferably be guanidine hydrochloride.

(13) Preferably, the solid phase bondable to nucleic acids may be a substance containing silicon dioxide.

(14) In a further aspect, the invention provides apparatus for the recovery of nucleic acids from a material containing nucleic acids, which is composed of a first means for mixing nucleic acids with an accelerator substance for the binding of nucleic acids to a solid phase, a second means for making the mixture in contact with a solid phase bondable to nucleic acids to form a nucleic acid-binding solid phase, a third means for isolating the nucleic acid-binding solid phase from a liquid, a fourth means for washing the nucleic acid-binding solid phase with a solution containing an acetate, and a fifth means for eluting the nucleic acids from the solid phase.

(15) The invention provides in yet another aspect apparatus for the recovery of nucleic acids from a material containing nucleic acids, which is composed of: a first pipetter for discharging an accelerator substance for the binding of nucleic acids to a solid phase, a solid phase bondable to nucleic acids, a washing solution for removing the accelerator substance from the solid phase, and a liquid for eluting nucleic acids from the solid phase, separately and in turn, into a chamber encasing a nucleic acid-containing material and for stirring the liquid mixture in the chamber, an isolating means for isolating the solid phase from the liquid phase in the chamber, a second pipetter for aspirating the liquid phase isolated by the isolating means from the chamber, and a control means for controlling operations of the first pipetter, the isolating means and the second pipetter, wherein the liquid which has been eluted from the solid phase by an eluent for eluting nucleic acids and isolated by the isolating means as a liquid phase is aspirated by the second pipetter, and an aqueous solution containing the nucleic acids is purified from the aspirated liquid.

When guanidine hydrochloride (hereinafter briefly referred to as GuHCl) is used as the accelerator substance for the binding of nucleic acids to a solid phase in step 1 of the above methods, such effects on absorbance at 260 nm as to adversely affect the assay of the purity or quantity of nucleic acids can be markedly reduced.

As the solid phase bondable to nucleic acids in step 2, any substance containing silicon oxide such as glass beads, silica powder, quartz filter paper, quartz wool or crushed products of these substances, diatomaceous earth and the like can be employed. When the solid phase has a particle size ranging from about 1 to about 100 μm, a practically sufficient binding of nucleic acids to the solid phase can be obtained in several minutes to ten minutes.

The use of diatomaceous earth can reduce a cost necessary for one treatment. When a stirring procedure is also employed for enhancing the contact probability of nucleic acid and the solid phase while depending on the specific gravity of the particle to be used, the reaction time for binding can be shortened and the reproducibility can be enhanced.

A bond form/free form isolation (B/F isolation) technique generally used in immunoassay devices utilizing an antigen-antibody reaction can be used as the isolating means for isolating the solid phase from a liquid in step 3, and known technologies in immunoassay devices can be exploited.

The step for washing the nucleic acid-binding solid phase with a solution containing an acetate or potassium chloride, or a mixture of an aqueous solution of a salt and an alcohol in step 4 can provide washing of the solid phase while maintaining the binding of nucleic acids to the solid phase. Accordingly, contaminants can be removed at a practically sufficient level without cooling when step 4 is divided into step 4a and step 4b, using GuHCl as the washing solution in step 4a and using a 40% ethanol aqueous solution containing 10 mmol/liter or more of potassium acetate as the washing solution in step 4b.

When a solution containing an alcohol is employed in step 4b, the addition of step 6 for removing the alcohol component after step 5 can prevent the contamination of alcoh in a final purified solution of nucleic acids.

According to a further aspect of the present invention, there is provided a method for and an apparatus for the recovering nucleic acids which enable a nucleic acid to be speedily simply recovered, with high purity and low cost, from materials containing nucleic acids and which enable nucleic acid components of specific sequence to be automatically recovered from biological samples. This aspect can be achieved by the following characteristics.

In the method of the present invention, a nucleic acid is recoverable by bringing a nucleic acid component-containing solution into contact in a pipeline with a solid phase bondable to the nucleic acid component. More specifically, this method comprises: a first step in which a mixed solution is prepared, the mixed solution being composed of a solution containing an objective nucleic acid component having a specific sequence and distributed in containers and an accelerator substance placed in the containers and acting to accelerate bonding of the nucleic acid component to a solid phase bondable to the latter component; a second step in which the mixed solution is contacted with the solid phase disposed in a pipeline by suctioning the mixed solution in the pipeline; a third step in which the solid phase is separated from a non-bondable component having not bonded thereto by discharging the mixed solution from the pipeline; a fourth step in which the solid phase is washed by suctioning a washing solution in the pipeline and then discharging the same therefrom; and a fifth step in which a nucleic acid component of a specific sequence is eluted from the solid phase by suctioning an eluting solution in the pipeline and then discharging the same therefrom.

BRIEF DESCRIPTION OF THE DRAWINGS

These and other features, objects and advantages of the present invention will become apparent upon a consideration of the following detailed description of the invention when read in conjunction with the drawings, in which.

DESCRIPTION OF THE PREFERRED EMBODIMENT

Embodiment 1

Figure 1:
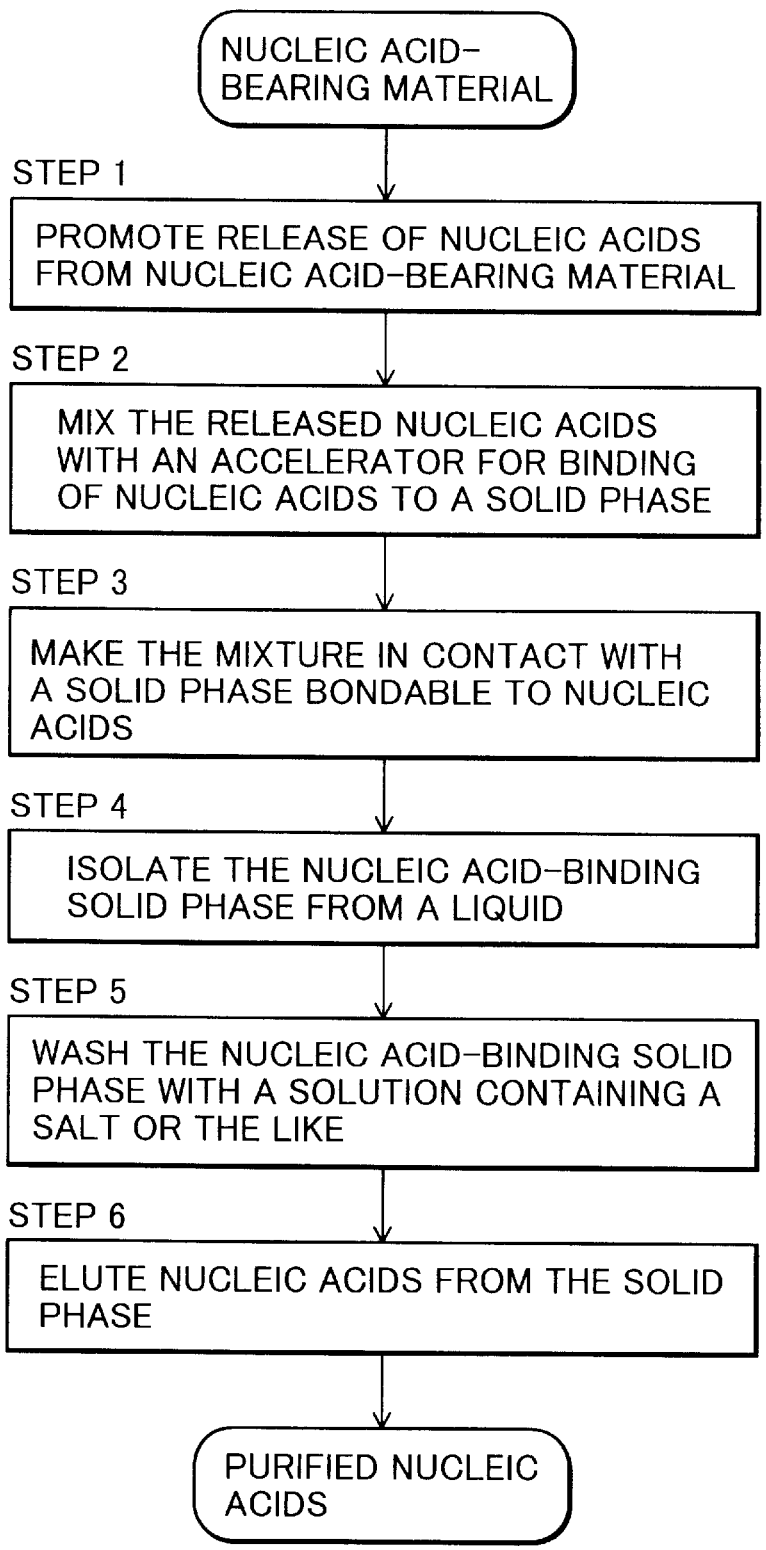
FIG. 1 is an operating flow chart for the recovery of nucleic acids according to a first embodiment of the invention.

Recovery of nucleic acids using an aqueous solution of an acetate at a concentration of 1 mol/liter or the like in the washing step Nucleic acids were recovered from an aqueous solution containing nucleic acids according to the flow chart in FIG. 1 in the following manner. A nucleic acid-containing material obtained by diluting a commercially available purified pBR322 DNA with a Tris-EDTA (hereinafter referred to as TE) buffer (pH of 7.4) was used.

In this case, nucleic acids were already free in the material, and step 1 for promoting the release of nucleic acids from the material was omitted. As the accelerator substance generally used in step 1, there may be mentioned surfactant, enzymes and others. The means for promoting the release of nucleic acids from the nucleic acid-containing material includes a heating means and a means of applying ultrasonic energy, for example.

In step 2 for mixing the released nucleic acids with an accelerator substance for the binding of nucleic acids to a solid phase, 900 μl of a 6 mol/liter GuHCl solution was added to 100 μl of the above aqueous solution containing nucleic acids and stirred in a 1.5-ml reactor.

Step 3 for making the mixture in contact with a solid phase bondable to nucleic acids was carried out by adding 100 mg of glass beads as the solid phase to the mixture and stirring the resultant mixture at room temperature by a rotary mixer to make the solid phase in contact with a liquid to form a nucleic acid-binding solid phase.

In the fourth step for isolating the nucleic acid-binding solid phase from a liquid, the mixture was centrifuged at 15,000 g for 1 minute with a centrifuge to give a sediment of the solid phase and the supernatant was discarded.

Step 5 for washing the nucleic acid-binding solid phase with a solution containing an acetate or the like was conducted by suspending the solid phase in a 1 mol/liter aqueous solution of an acetate or other reagents indicated in Table 1, and discarding the supernatant.

In step 6 for eluting nucleic acids from the solid phase, a TE buffer (pH 8.0) was added to the solid phase and heated at 60° C. for 1 minute for elution, and the elute was centrifuged at 15,000 g for 1 minute to give a supernatant. A part of the supernatant was subjected as a sample to electrophoresis using a 0.8% agarose gel as a support and subsequently to ethiodium bromide staining, and the intensities of individual bands were converted into numbers by densitography so as to calculate the recovery based on the amount of nucleic acids in step 1.

The results are shown in Table 1. These results demonstrate that the use of ammonium chloride or potassium acetate provides efficient maintenance of nucleic acids in the washing as compared to the use of sodium chloride.

TABLE 1

| Salt | Recovery |
| --- | --- |
| Lithium chloride | 1.8% |
| Sodium chloride | 76.3% |
| Potassium chloride | 43.0% |
| Ammonium chloride | 81.0% |
| Sodium acetate | 12.5% |
| Potassium acetate | 81.9% |
| Ammonium acetate | 5.2% |
| Tris buffer | 0.9% |

As described above, the method according to Embodiment 1 of the invention includes a step 1 for promoting the release of nucleic acids from a nucleic acid-bearing material, a step 2 for mixing the released nucleic acids with an accelerator substance for the binding of nucleic acids to a solid phase, a step 3 for making the mixture in contact with a solid phase bondable to nucleic acids to form a nucleic acid-binding solid phase, a step 4 for isolating the solid phase from a liquid, a step 5 for washing the nucleic acid-binding solid phase with a solution containing ammonium chloride or potassium acetate, and a step 6 for eluting nucleic acids from the solid phase.

Embodiment 1 of the invention provides a method for the recovery of nucleic acids which can rapidly and easily recover high-purity nucleic acids from a material containing nucleic acids at a high recovery yield without reducing the yield. In other words, nucleic acids at a suitable purity for genetic tests or gene analyses can be rapidly and easily recovered without the use of hazardous substances.

In addition, this embodiment provides a method for the recovery of nucleic acids, which is suitable for apparatus for automatic recovery of nucleic acid components in a biological sample, because it does not require the use of volatile substances or substances deteriorating the apparatus.

Accordingly, it provides a method for the recovery of nucleic acids, which is desirably applicable to apparatus for the automatic recovery of plasmid DNAs from *E coli*.

Embodiment 2

Figure 2:
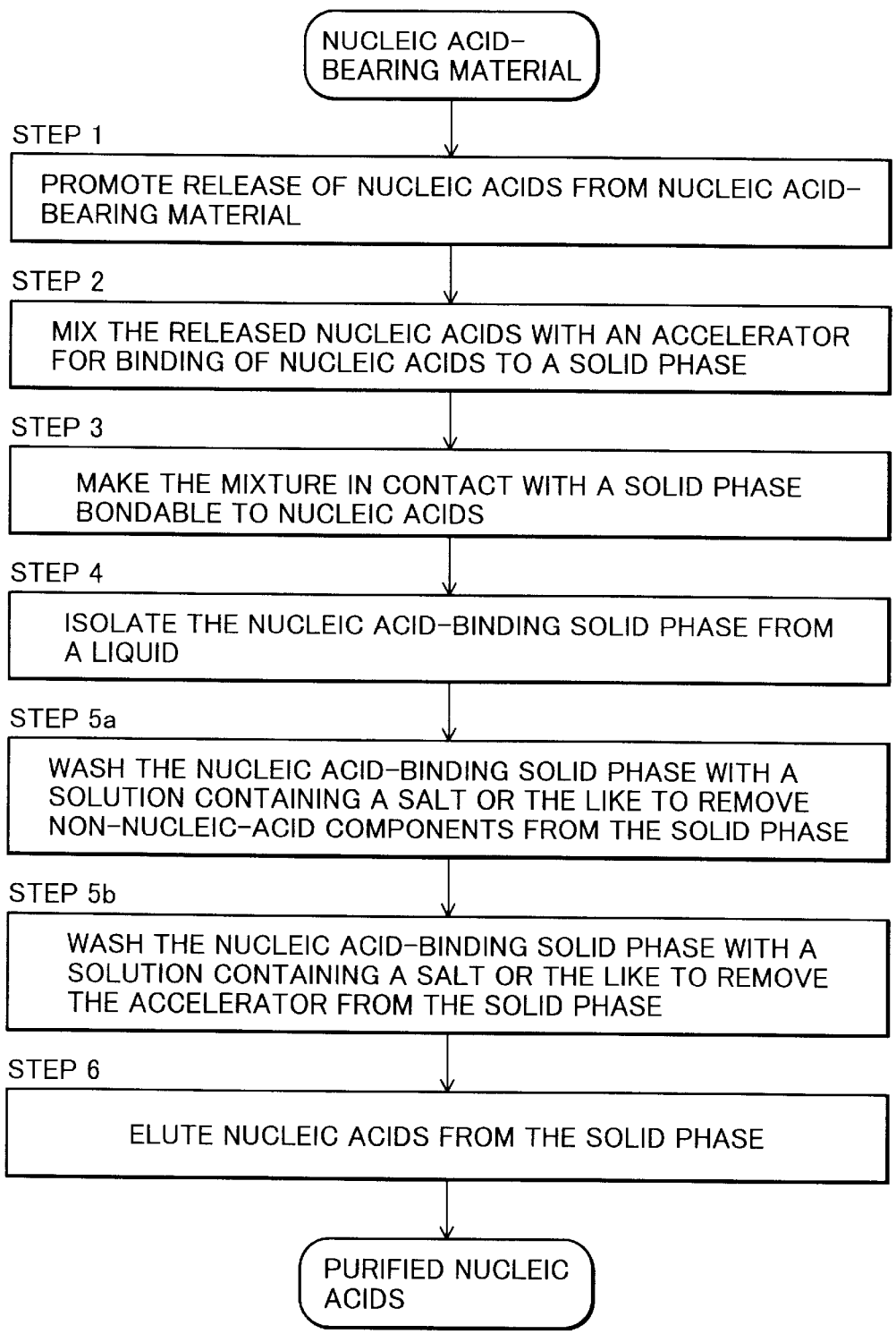
FIG. 2 is an operating flow chart for the recovery of nucleic acids inclusive of a washing step with a solution containing potassium acetate or the like according to a second embodiment of the invention.

Recovery of nucleic acids using a solution containing potassium chloride or potassium acetate in the washing step Nucleic acids were recovered from an aqueous solution containing nucleic acids in accordance with the flow chart shown in FIG. 2. Steps 1, 2, 3, 4 and 6 in the flow chart in FIG. 2 are similar to those in the flow chart of FIG. 1, whereas step 5 in FIG. 1 is divided into steps 5a and 5b in FIG. 2.

A material containing nucleic acids obtained by diluting a commercially available purified pBR322 DNA with a TE buffer (pH 7.4) was employed in Embodiment 2, as similar to Example 1.

The description of steps 1 to 4 is omitted because these steps are the same as those of FIG. 1.

Step 5a is a step for removing non-nucleic-acid components from the solid phase by washing the nucleic acid-binding solid phase with a solution containing a salt. The solid phase was washed by suspending the solid phase in 1,000 µl of a 6 mol/liter guanidine hydrochloride (GuHCl) solution, centrifuging the suspension at 15,000 g for 1 minute to obtain a sediment of the solid phase and discarding the supernatant.

In step 5b for washing the nucleic acid-binding solid phase with a solution containing a salt to remove the accelerator substance from the solid phase, the solid phase was suspended respectively in aqueous solutions of NaCl, KCl, NaOAc (sodium acetate) or KOAc (potassium acetate) having different concentrations and the supernatant was discarded.

Step 6 was conducted as follows: A TE buffer (pH 8.0) was added to the solid phase, the mixture was heated at 60° C. for 1 minute for elution, the elute was centrifuged at 15,000 g for 1 minute to obtain a supernatant, a part of the supernatant as a sample was subjected to electrophoresis with the use of a 0.8% agarose gel as a support, then to ethidium bromide staining, the intensities of individual bands were converted into numbers by densitography, and the recovery was calculated based upon the amounts of nucleic acids in step 1.

Figure 6:
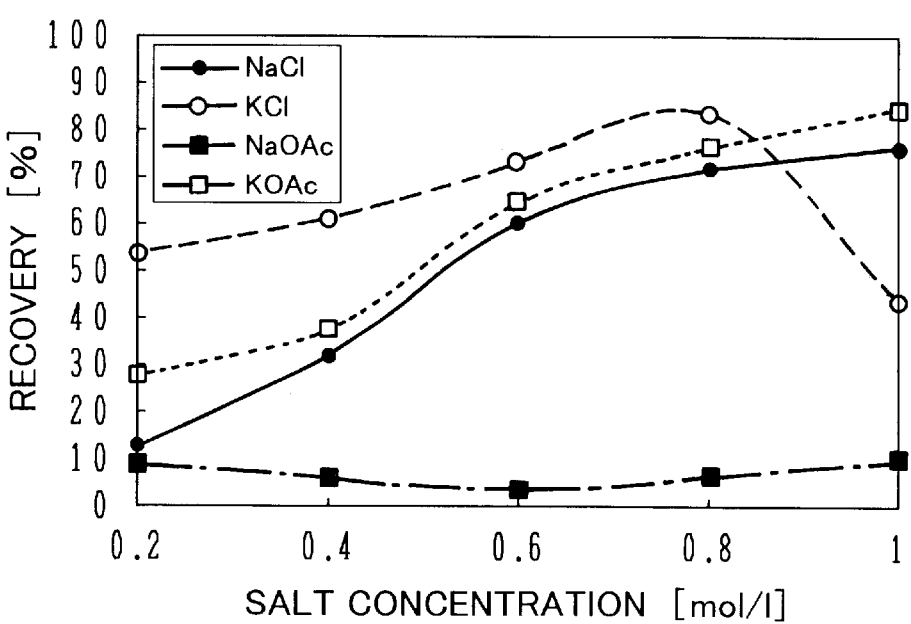
FIG. 6 is a graphical diagram illustrating the results of the washing step according to the second embodiment of the invention.

The results are set forth in FIG. 6. When NaCl or KOAc was used at a concentration of 500 mmol/liter or more, a recovery of equal to or more than 50% was obtained, whereas when KCl was used at a concentration of 200 mmol/liter or more, a recovery of equal to or more than 50% was obtained. These results demonstrate that the use of KCl or KOAc provides, at least, more efficient recovery of nucleic acids than the use of NaCl at least a concentration of 800 mmol/liter or less.

As described above, Embodiment 2 according to the invention where KCl or KOAc is used for washing non-nucleic acid components or the like can obtain similar advantages to Embodiment 1.

Embodiment 3

Figure 3:
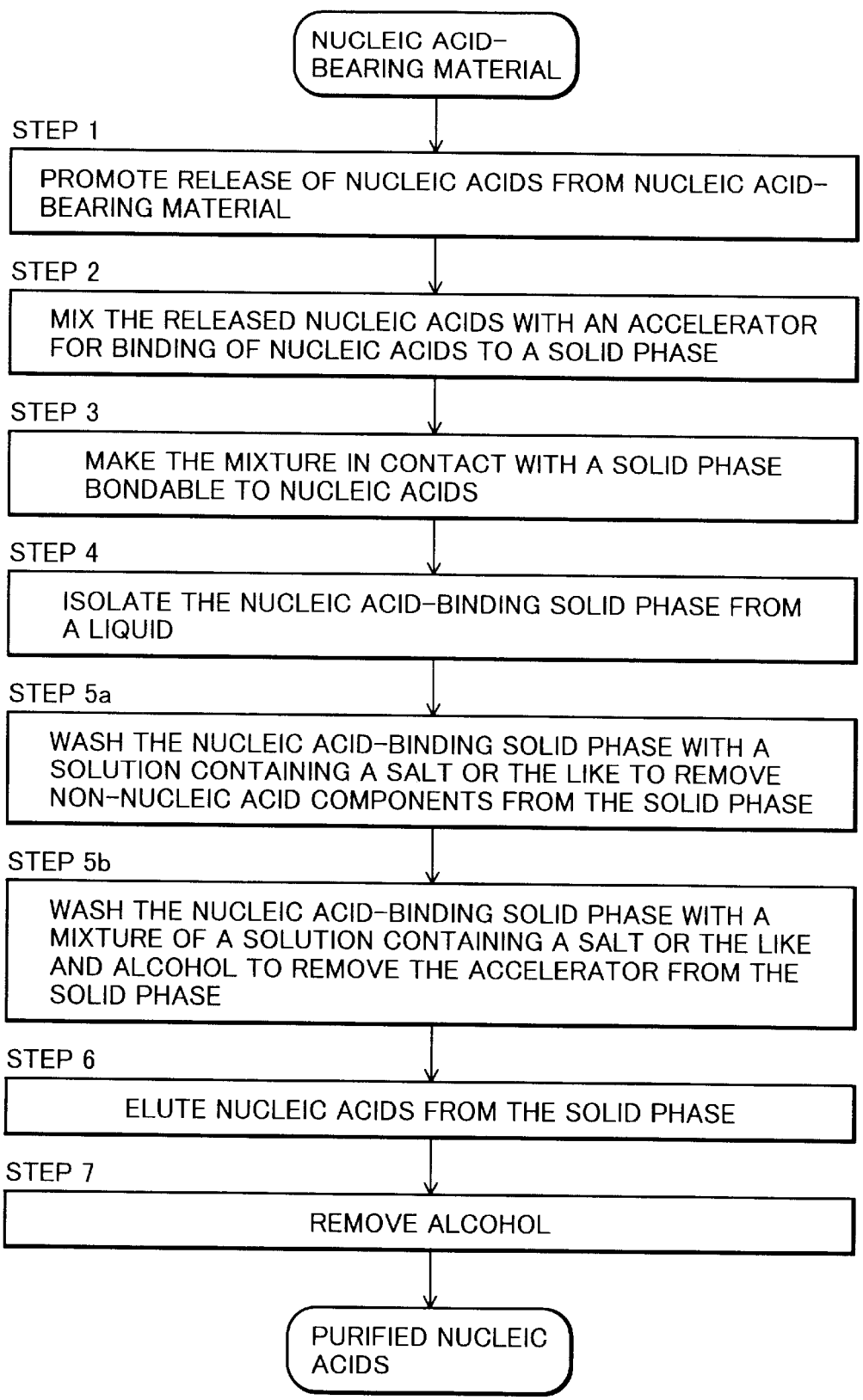
FIG. 3 is an operating flow chart for the recovery of nucleic acids inclusive of a washing step according to third, fourth, fifth and sixth embodiments of the invention.

Recovery of nucleic acids using a solution containing sodium acetate in the washing step Nucleic acids were recovered from an aqueous solution containing nucleic acids in accordance with the flow chart shown in FIG. 3. Steps 1, 2, 3, 4, 5a and 6 in the flow chart of FIG. 3 are the same as in the flow chart of FIG. 2, hence the description of steps 1 to 5a is omitted.

Step 5b was conducted by suspending the solid phase in aqueous solutions of 40% ethanol and KOAc or NaCl having different concentrations, and discarding the supernatant. Step 6 was carried out by adding a TE buffer (pH 8.0) to the solid phase, heating the mixture at 60° C. for 1 minute for elution, centrifuging the elute at 15,000 g for 1 minute to give a supernatant. In the step 7 for removing alcohol, ethanol was removed by heating at 60° C. to give an aqueous solution of purified nucleic acids.

A part of the solution was subjected as a sample to electrophoresis using a 0.8% agarose gel, and then to ethidium bromide staining, the intensity of each band was converted into numbers by densitography, and the recovery was calculated based upon the amounts of nucleic acids in the step 1.

Figure 7:
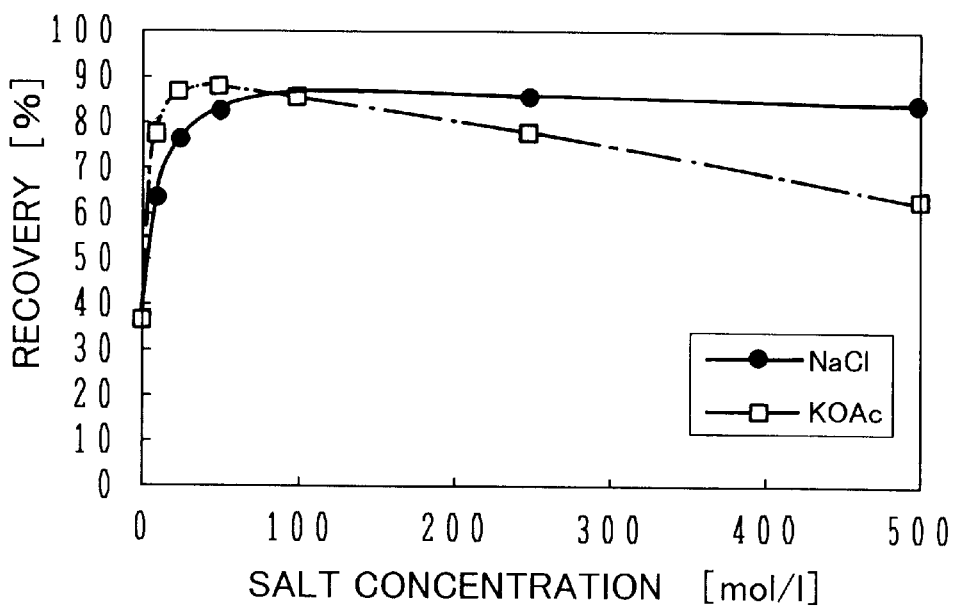
FIG. 7 is a graphical diagram showing the results of the washing step according to the third embodiment invention.

The results are indicated in FIG. 7. When used in combination with 40% ethanol, the use of KOAc can more efficiently recover nucleic acids than the use of NaCl at a concentration ranging from 10 mmol/liter to 25 mmol/liter.

According to Embodiment 3 of the invention, similar advantages to Embodiment 1 can be obtained with the use of KOAc at a concentration ranging from 10 mmol/liter to 25 mmol/liter.

Embodiment 4

Recovery of nucleic acids with the use of a combination of ethanol with solutions of sodium acetate or sodium chloride at different ethanol concentrations in the washing step In accordance with the flow chart indicated in FIG. 3, nucleic acids were recovered from an aqueous solution containing nucleic acids. Steps 1, 2, 3, 4, 5a and 6 in the flow chart of FIG. 3 are the same as in the flow chart of FIG. 2, hence the description of the steps 1 to 5a is omitted.

Step 5b is a step for removing the accelerator substance from the solid phase by washing the nucleic acid-binding solid phase with a solution containing a salt. Step 5b was conducted by suspending the solid phase in 25 mmol/liter or 50 mmol/liter of KOAc or 50 mmol/liter or 100 mmol/liter of NaCl in combination with different concentrations of ethanol, and discarding the supernatant.

Step 6 was carried out by adding a TE buffer (pH 8.0) to the solid phase, heating the mixture at 60° C. for 1 minute for elution, centrifuging the elute at 15,000 g for 1 minute to give a supernatant. In step 7 for removing alcohol, ethanol was removed by heating the mixture at 60° C. to give an aqueous solution of purified nucleic acids.

A part of the solution was subjected as a sample to electrophoresis using a 0.8% agarose gel, and then to ethidium bromide staining, the intensity of each band was converted into numbers by densitography, and the recovery was calculated based upon the amounts of nucleic acids in step 1.

Figure 8:
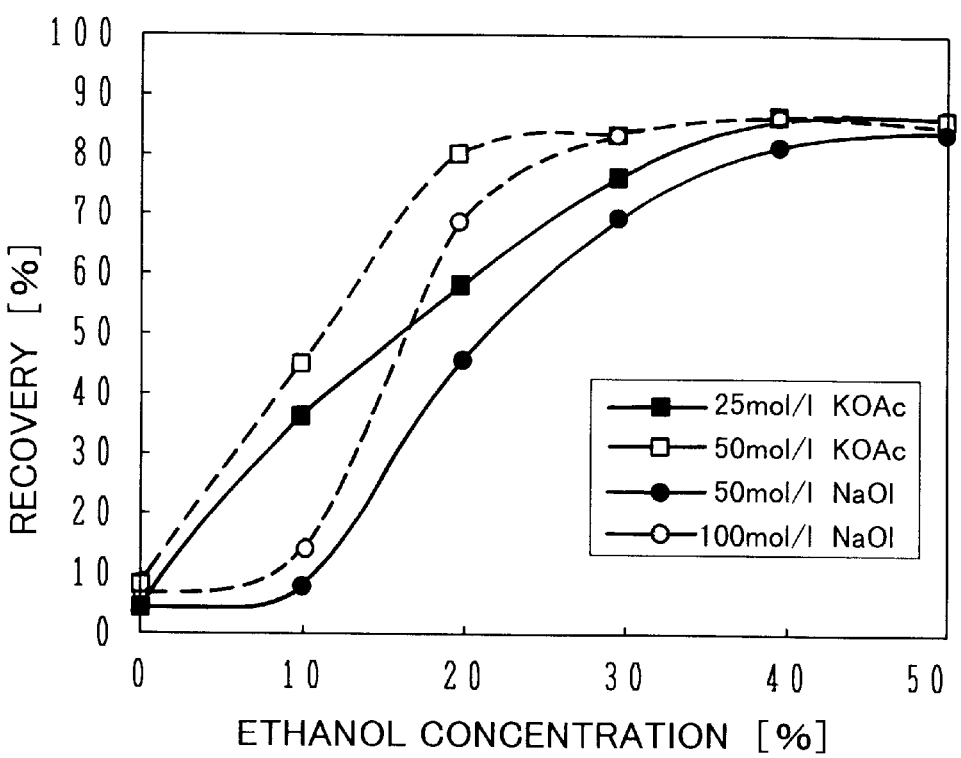
FIG. 8 is a graphical diagram indicating the results of the washing step according to the fourth embodiment of the invention.

The results are shown in FIG. 8. The combination use of 50 mmol/liter or more of KOAc or 100 mmol/liter or more of NaCl with ethanol can effectively prevent the recovery rate from falling when the concentration of ethanol varies.

As mentioned above, Embodiment 4 of the invention can provide similar advantages to Embodiment 1. Incidentally, the method according to Embodiment 4 does not invite the same disadvantages as conventional equivalents even though ethanol is employed, because ethanol is used in combination with 25 mmol/liter or 50 mmol/liter of KOAc or 50 mmol/liter or 100 mmol/liter of NaCl.

Embodiment 5

Recovery of nucleic acids added to serum

Nucleic acids added to serum were recovered in accordance with the flow chart shown in FIG. 3.

A sample obtained by adding a commercially available purified pBR322 DNA to human serum was used. Nucleic acids in this sample were already free, but sodium dodecyl sulfate (SDS) was added to the sample in step 1 as measures against nuclease.

Steps 2 to 5a are the same as in Embodiment 4, and the description of these steps is omitted.

In step 5b, the solid phase was suspended in a 50% ethanol aqueous solution containing 50 mmol/liter of KOAc and the supernatant was discarded.

Step 6 was carried out by adding a TE buffer (pH 8.0) to the solid phase, heating the mixture at 60° C. for 1 minute for elution, and centrifuging the elute at 15,000 g for 1 minute to give a supernatant. In step 7 for removing alcohol, ethanol was removed by heating at 60° C. to give an aqueous solution of purified nucleic acids.

A part of the solution was subjected as a sample to electrophoresis using a 0.8% agarose gel, and then to ethidium bromide staining, the intensity of each band was converted into numbers by densitography, and the recovery rate was calculated based upon the amounts of nucleic acids in step 1. The recovery was 70% and $A_{260}/A_{280}$ was 1.90. The total time required for steps 1 to 7 was about 30 minutes.

The method according to Embodiment 5 can also provide similar advantages to Embodiment 1 mentioned above. Even though ethanol is used in Embodiment 5, disadvantages as in conventional equivalents do not occur because a 50% ethanol aqueous solution containing 50 mmol/liter of KOAc is employed.

Embodiment 6

Recovery of plasmid DNAs from cultured recombinant *E. Coli*

Plasmid DNAs were recovered from cultured recombinant *E. coli* in accordance with the flow chart of FIG. 3. As a sample, *E. coli* obtained by integrating pBR322 DNA into *E. coli* HB101 in a genetic engineering manner. The sample was obtained in the following manner: *E. coli* was cultured in 1 ml of LB medium at 37° C. for one night and cells were collected by centrifugation, then suspended in 100 μl of a 0.15 mol/liter solution of NaCl to give a sample.

In step 1, a solution containing 50 mmol/liter of glucose, 10 mmol/liter of EDTA and 25 mmol/liter of Tris-HCl buffer (pH 8.0) with 8 mg/ml of lysozyme was added to the sample for destroying peptidoglycan in the cell wall of *E. coli*.

Further, a solution of 0.2 mol/liter of NaOH and 1% of SDS was added to the resultant mixture for the release of nucleic acids. To this solution was added a 5 mol/liter potassium acetate solution to give an aqueous solution containing nucleic acids.

A total of 1,000 μl of a 6 mol/liter GuHCl solution was added to the above aqueous solution and stirred in step 2.

Step 3 was conducted by adding 150 mg of glass beads as a solid phase bondable to nucleic acids to the above mixture and stirring the resultant mixture at room temperature by a rotary mixer to make the solid phase in contact with a liquid and to form a nucleic acid-binding solid phase.

In step 4 for isolating the nucleic acid-binding solid phase from a liquid, the mixture was subjected to centrifugation at 15,000 g for 1 minute to give a sediment of the solid phase, and the supernatant was discarded.

Step 5a was carried out for washing the solid phase by suspending the solid phase in 1,000 μl of a 6 mol/liter GuHCl solution, centrifuging the suspension at 15,000 g for 1 minute to give a sediment of the solid phase, and discarding the supernatant.

In step 5b, the solid phase was suspended in a 50% ethanol aqueous solution containing 50 mmol/liter of KOAc, and the supernatant was discarded.

Step 6 was carried out by adding a TE buffer (pH 8.0) to the solid phase, heating the mixture at 60° C. for 1 minute for elution, centrifuging the elute at 15,000 g for 1 minute to give a supernatant. In step 7 for removing alcohol, ethanol was removed by heating at 60° C. to give an aqueous solution of purified nucleic acids. A part of the solution was subjected as a sample to electrophoresis using a 0.8% agarose gel, and then to ethidium bromide staining to give electrophoresis bands of nucleic acids. As a result, bands of plasmid DNA and rRNA were determined in comparison with a molecular weight marker which was subjected to electrophoresis simultaneously.

The $A_{260}/A_{280}$ was 1.96 at this step. The yield of plasmid DNAs was 4.5 μg as calculated from absorbencies of $A_{260}$ after treatments with ribonuclease and ethanol precipitation. The total time required for the steps 1 to 7 was about 45 minutes.

The method according to Embodiment 6 can provide similar advantages to Embodiment 1 mentioned above. Even though ethanol is used in Embodiment 6, disadvantages as in conventional equivalents are not invited, because a 50% ethanol aqueous solution containing 50 mmol/liter of KOAc is employed.

Embodiment 7

Figure 9:
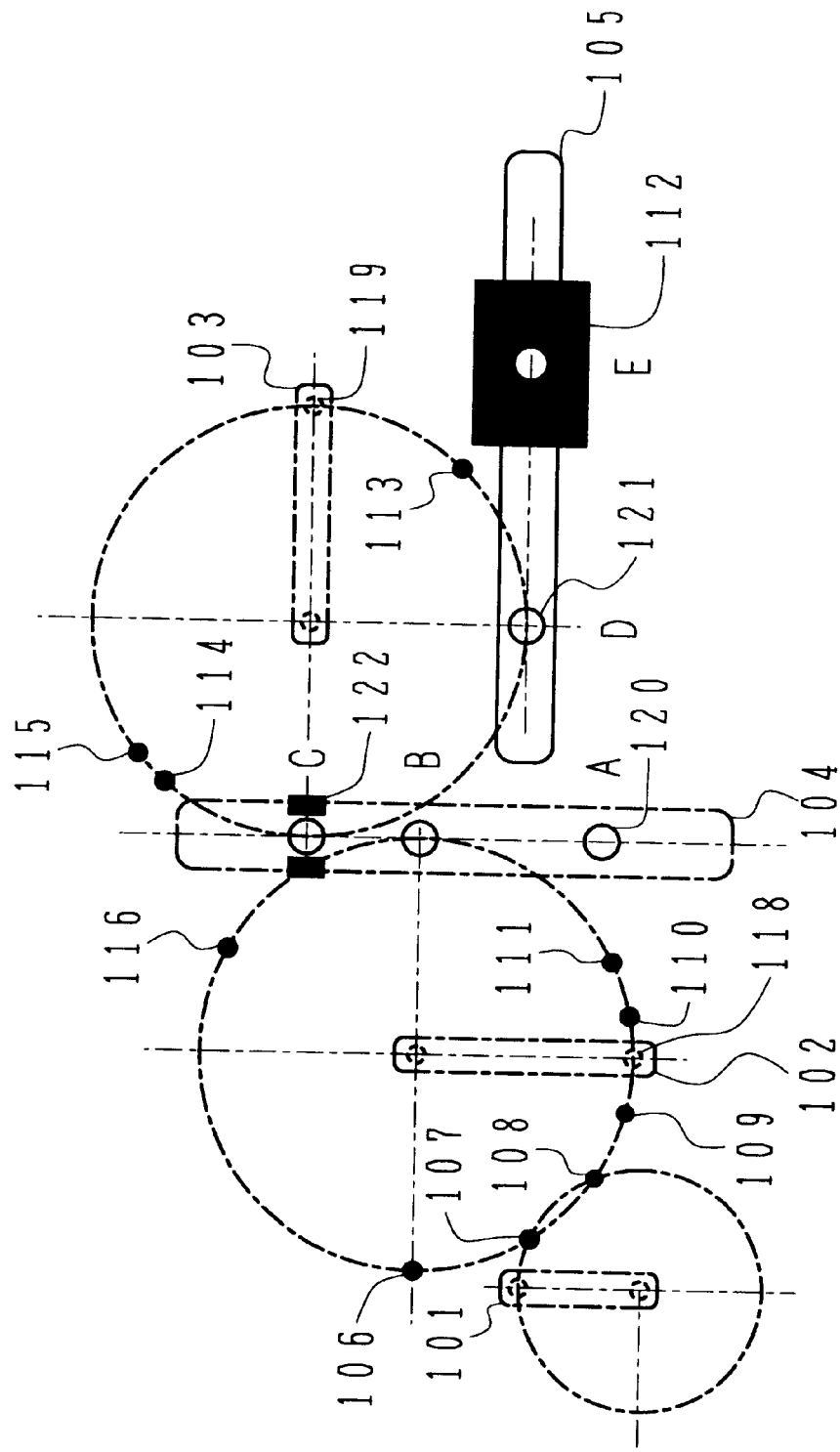
FIG. 9 is a plan view of a layout of apparatus for the recovery of nucleic acids as a seventh embodiment of the invention.
Figure 10:
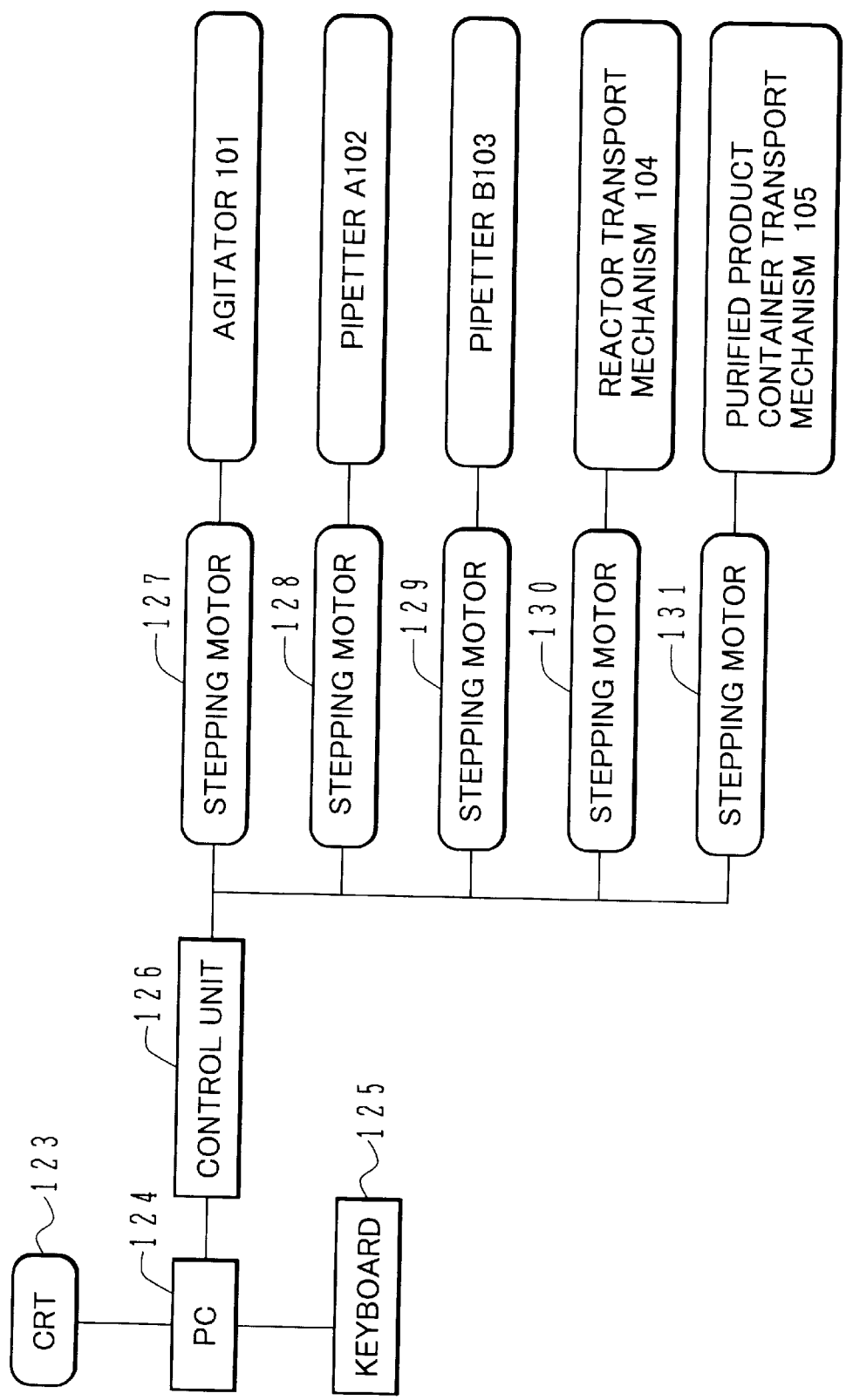
FIG. 10 is a schematic block diagram illustrating apparatus for the recovery of nucleic acids.

Recovery of DNAs added to serum by an automatic device for the recovery of nucleic acids FIG. 9 is a plan view of a layout of an apparatus (automatic device) for the recovery of nucleic acids as Embodiment 7 of the invention; FIG. 10 is a schematic block diagram illustrating the apparatus; and FIG. 11 is a simplified drawing of the outside of the apparatus.

In FIG. 10, a personal computer (PC) 124 as an operation control unit is connected to a keyboard 125 as a control panel for input of operation conditions of the apparatus or information on test samples, a CRT 123 as a display for showing input information, alarm information or others, and a mechanical control unit 126 for controlling each mechanical unit of the apparatus. The personal computer 124 includes a memory for holding data and programs.

The mechanical control unit 126 controls a stepping motor 127 for moving an agitator 101 circumferentially and vertically, and a stepping motor 128 for moving a pipetter A 102 circumferentially and vertically. The mechanical control unit 126 also controls a stepping motor 129 for circumferentially and vertically moving a pipetter B 103, a stepping motor 130 for horizontally moving a reactor transport mechanism 104, and a stepping motor 131 for horizontally moving a transport mechanism 105 for a purified product container.

Figure 11:
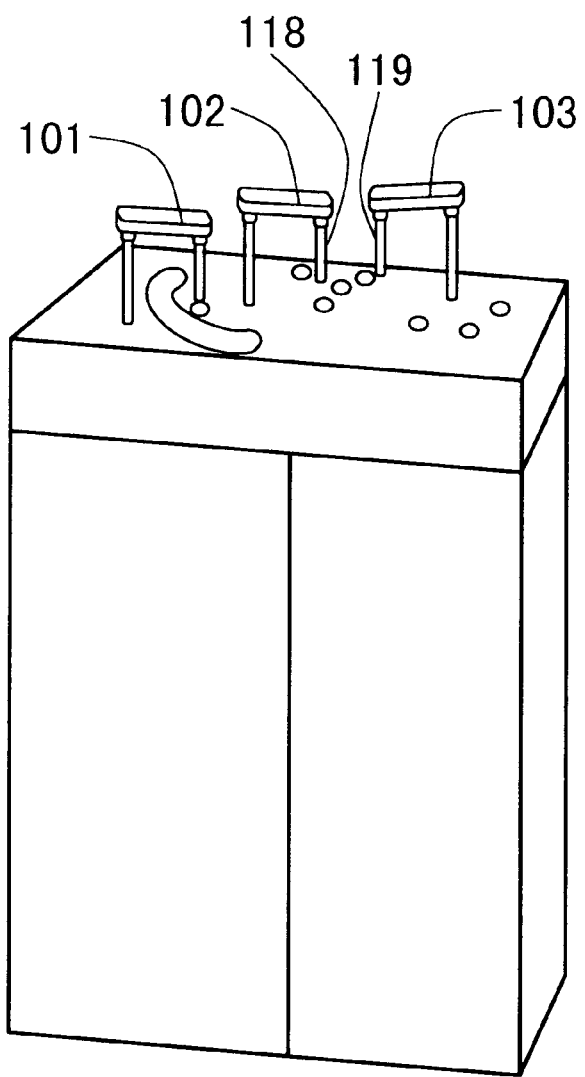
FIG. 11 is a simplified outside drawing of apparatus for the recovery of nucleic acids.

The agitator 101 as shown in FIGS. 9 to 11 is movable circumferentially and vertically, and movable between an inlet 107 for particles and a washing position 108 as a function of the mechanical control unit 126. The pipetter A 102 and the pipetter B 103 are movable circumferentially and vertically, and respectively have a nozzle 118 and a nozzle 119 for mounting a disposable tip.

The reactor transport mechanism 104 can transport a reactor 120 to point A, B or C as a function of the mechanical control unit 126, and a permanent magnet 122 is placed on both sides of the point C in such a shape as to fit the size of the reactor 120. The transport mechanism 105 is capable of transporting a purified product container 121 to points D and E as a function of the mechanical control unit 126.

Nucleic acids added to serum were recovered by the apparatus illustrated in FIG. 9 in accordance with the flow chart of FIG. 3.

A sample obtained by adding a commercially available purified pBR322 DNA to human serum was dispensed to the reactor 120 in a given volume, and the reactor was placed at the point A. Although the nucleic acids in this sample were already free, SDS was added to the sample in step 1 for measures against nuclease.

In step 2, the reactor 120 was moved to the point B by the reactor transport mechanism 104, and the pipetter A 102 was moved to a tip mount position 106 by rotating circumferentially to mount a tip on the nozzle 118. Subsequently, the pipetter A 102 was moved to an inlet 109 to aspirate 900 $\mu$l of a 8 mol/liter GuHCl solution relative to 100 $\mu$l of the aqueous solution containing nucleic acids.

The pipetter A 102 was then moved to the point B so as to discharge GuHCl into the reactor 120. The aspiration-discharging operation was then repeated several times for stirring. The pipetter A 102 was then moved to a tip-discarding position 116 so as to discard the tip from the nozzle 118.

In step 3, magnetic particles in a liquid was used as a solid phase bondable to nucleic acids, and the liquid was stirred by the agitator 101 from the inlet 107, whereas a new tip was mounted to the nozzle 118 of the pipetter A 102 at the tip mount position 106. The stirred liquid containing magnetic particles was aspirated through the new tip. The pipetter A 102 was then moved to the point B, and the content of the tip was discharged into the reactor 120. The aspiration-discharging procedure was repeated for stirring. The agitator 101 was moved to the washing position 108 and washed, whereas the pipetter A 102 was moved to the tip discarding position 116 to discard the tip from the nozzle 118.

Step 4 was conducted for isolating the nucleic acid-bearing solid phase from a liquid in the following manner: Initially, the reactor 120 was moved from the point B to the point C by the reactor transport mechanism 104 and magnetic particles in the reactor 120 were attracted onto the side wall of the reactor by means of the permanent magnet 122. Next, the pipetter B 103 was moved to a tip mount position 113 by rotation to mount a tip on the nozzle 119, and then moved to the point C so as to aspirate a liquid phase in the reactor 120. The pipetter B was then moved to a solution-discarding position 114 so as to discard the solution from the tip, and moved to a tip-discarding position 115 to discard the tip from the nozzle 119.

In step 5a, the reactor 120 was moved from the point C to the point B by means of the reactor transport mechanism 104, and the pipetter A 102 was moved to the tip mount position 106 to mount a tip on the nozzle 118. Subsequently, the pipetter A 102 was moved to an inlet 111 to aspirate the GuHCl solution at a given volume, and then moved to the point B to discharge the GuHCl solution into the reactor 120. After stirring the mixture by the aspiration-discharging operation, the pipetter was moved to the tip-discarding position 116 to discard the tip from the nozzle 118.

Subsequently, the reactor 120 was moved from the point B to the point C by means of the reactor transport mechanism 104, and the magnetic particles in the reactor 120 were attracted onto the side wall of the reactor by the permanent magnet 122. The pipetter B 103 was then moved to the tip mount position 113 by rotation to mount a tip on the nozzle 119, and then moved to the point C to aspirate a liquid phase in the reactor 120. The pipetter B was then moved to the solution-discarding position 114 so as to discard the solution from the tip, and moved to the tip-discarding position 115 to discard the tip from the nozzle 119.

In step 5b, the reactor 120 was moved from the point C to the point B by the reactor transport mechanism 104. Next, the pipetter A 102 was moved to the tip mount position 106 to mount a tip to the nozzle 118, and moved to an inlet 110 to aspirate a given volume of a 50% ethanol aqueous solution containing 50 mmol/liter of KOAc. Subsequently, the pipetter was moved to the point B to discharge the ethanol solution into the reactor 120. After stirring the content of the reactor by the aspiration-discharging operation, the pipetter was moved to the tip-discarding position 116 to discard the tip from the nozzle 118.

Further, the reactor 120 was moved from the point B to the point C by the reactor transport mechanism 104 and magnetic particles in the reactor 120 were attracted onto the side wall of the reactor by means of the permanent magnet 122. Next, the pipetter B 103 was moved to the tip mount position 113 by rotation to mount a tip on the nozzle 119, and then moved to the point C so as to aspirate a liquid phase in the reactor 120. The pipetter was then moved to the solution-discarding position 114 so as to discard the solution in the tip, and moved to the tip-discarding position 115 to discard the tip from the nozzle 119. This step was further repeated a given number of times.

In step 6, the reactor 120 was moved from the point C to the point B by the reactor transport mechanism 104, and the pipetter A 102 was moved to the tip mount position 106 to mount a tip on the nozzle 118, then moved to the inlet 109 to aspirate a given volume of a TE buffer (pH 8.0) heated at 60° C., and moved to the point B. The heated TE buffer was then discharged into the reactor 120 to stir the contents by the aspiration-discharging operation, and the pipetter A was moved to the tip-discarding position 116 to discard the tip from the nozzle 118.

Subsequently, the reactor 120 was moved from the point B to the point C by the reactor transport mechanism 104, the magnetic particles in the reactor 120 were attracted onto the side wall of the reactor by the permanent magnet 122, and the pipetter B 103 was then moved to the tip mount position 113 by rotation to mount a tip on the nozzle 119. The pipetter was then moved to the point C to aspirate a liquid phase in the reactor 120 and moved to the point D to discharge the solution into the purified product container 121. This step was further repeated a given number of times.

In step 7, the purified product container 121 was moved to the position E on a heat block 112 at 60° C. by the transport mechanism 105, and heated for a given period to obtain an aqueous solution containing purified nucleic acids.

A part of the obtained solution was subjected as a sample to electrophoresis using a 0.8% agarose gel as a support, then to ethidium bromide staining. The intensities of individual bands were converted into numbers by densitography, and the recovery was calculated based upon the amounts of nucleic acids in step 1. The resultant recovery was 65%. The total time required for steps 1 to 7 was about 30 minutes.

As thus described, an apparatus for the recovery of nucleic acids can be obtained according to Embodiment 7 of the invention, by which nucleic acids can be rapidly and easily recovered at a high purity without deteriorating the yield. Even though ethanol is used in Embodiment 7, disadvantages as in conventional equivalents are not invited, because a 50% ethanol aqueous solution containing 50 mmol/liter of KOAc is employed.

The operation of the apparatus as described above is carried out by a program held in the memory of the personal computer 124. The program can also be executed by recording in a recording it medium such as a compact disc (CD) separately and reading from the recording medium. The recording medium can surely be taken out from the apparatus for recovery.

Next, a comparative example will be described for the comparison between the present invention and related art.

Comparative Example

Figure 4:
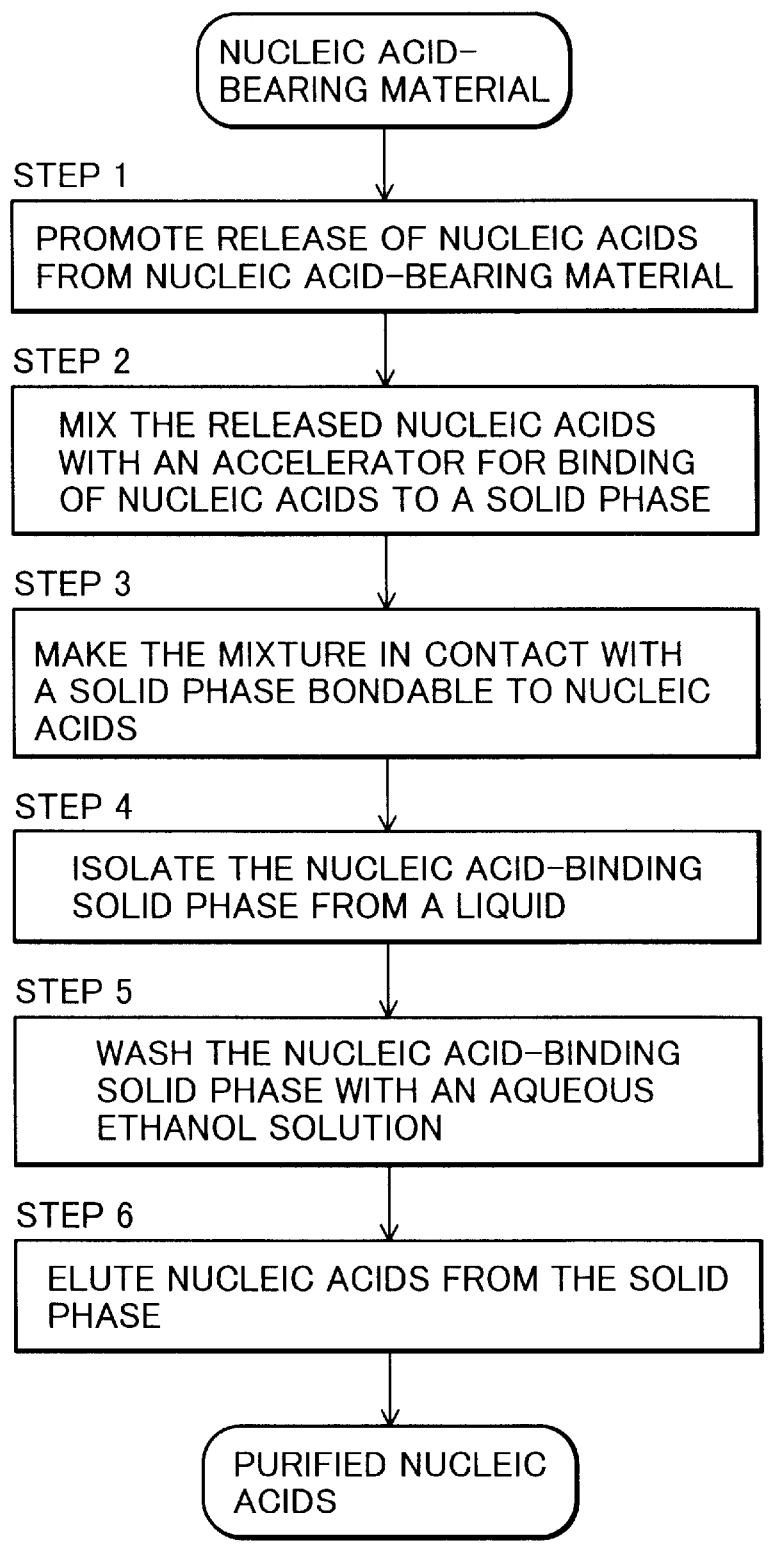
FIG. 4 is an operating flow chart inclusive of a washing step only with an aqueous ethanol solution according to conventional techniques for the recovery of nucleic acids.

Recovery of nucleic acids using only an aqueous ethanol solution in the washing step as in the case of conventional equivalents Nucleic acids were recovered from an aqueous solution containing nucleic acids in accordance with the flow chart of FIG. 4. A nucleic acid-bearing material obtained by diluting a commercially available pBR322 DNA with a TE buffer (pH 7.4) was used.

Step 1 for promoting the release of nucleic acids from a nucleic acid-bearing material was omitted, since the nucleic acids in the material were already free. Step 2 for mixing the free nucleic acids with an accelerator substance for binding of nucleic acids to a solid phase was conducted by adding 900 $\mu$l of a 6 mol/liter GuHCl solution to 100 $\mu$l of the aqueous solution of nucleic acids and stirring the mixture in a 1.5-ml reactor.

In step 3 for making the mixture in contact with a solid phase bondable to nucleic acids, 100 mg of glass beads as the solid phase was added to the mixture, and the resultant mixture was stirred at room temperature by a rotary mixer so as to make the solid phase in contact with a liquid and to form a nucleic acid-binding solid phase.

In step 4 for isolating the nucleic acid-binding solid phase from a liquid, the mixture was centrifuged at 15,000 g for 1 minute using a centrifuge to give a sediment of the solid phase, and the supernatant was discarded.

Step 5 for washing the nucleic acid-binding solid phase with an aqueous ethanol solution was carried out by suspending the solid phase respectively in aqueous ethanol solutions having different concentrations, centrifuging the suspension at 15,000 g for 1 minute to give a sediment of the solid phase, and discarding the supernatant.

Step 6 was conducted as follows: A TE buffer (pH 8.0) was added to the solid phase, the mixture was heated at 60° C. for 1 minute for elution, the elute was centrifuged at 15,000 g for 1 minute to obtain the supernatant, a part of the supernatant was subjected as a sample to electrophoresis with the use of a 0.8% agarose gel as a support, then to ethidium bromide staining, the intensities of individual bands were converted into numbers by densitography, and the recovery was calculated based upon the amounts of nucleic acids in step 1.

Figure 5:
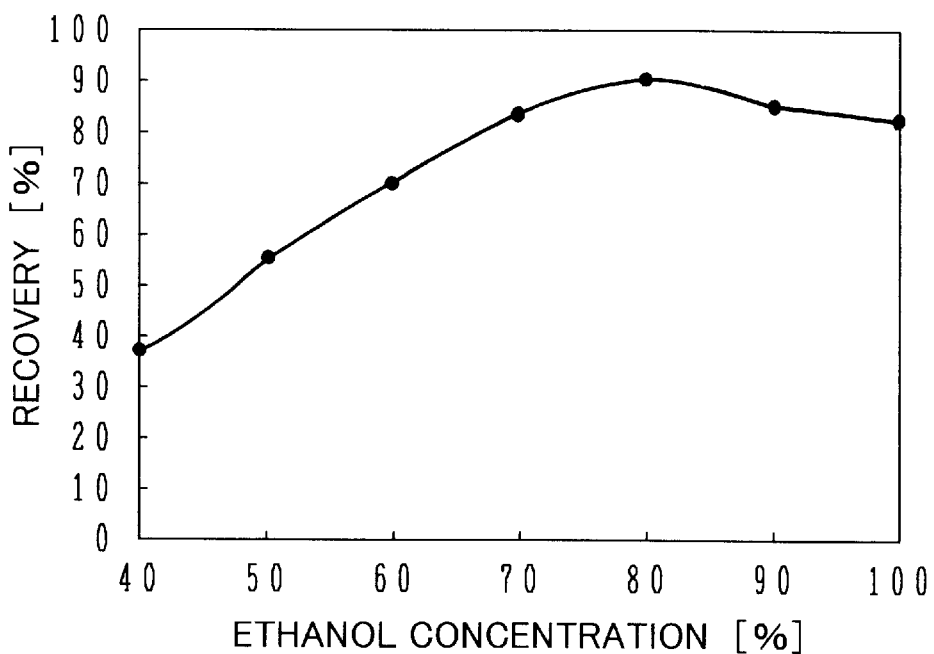
FIG. 5 is a graphical diagram illustrating the results of the washing step with ethanol according to conventional techniques.

The results are indicated in FIG. 5. It was confirmed that the recovery of nucleic acids decreases with its peak at an ethanol concentration of about 80%, that is, the recovery is maximized at an ethanol concentration of 80%. In such a method, however, the use of ethanol at a high concentration is required and ethanol is volatile as described above. Accordingly, when such an ethanol solution is mounted on an automatic device, the device requires a highly airtight chamber and a close-open mechanism of a lid and/or a cooling mechanism for preventing volatilization of ethanol, and this complicates the construction of the device.

On the contrary, the aforementioned Embodiments 1 to 7 according to the invention can provide methods and apparatus for the recovery of nucleic acids, by which nucleic acids having a high purity can be rapidly and easily recovered from a material containing nucleic acids without deteriorating the yield.

The present invention can be applied to any material containing nucleic acids, and the preferred material include, for example, whole blood, serum, expectoration, urine and other clinical samples, cultured cells, cultured bacteria and other biological samples, and nucleic acids retained on a gel after electrophoresis.

The methods according to the invention are also effective for materials containing DNA amplified enzymes and other reaction products or crude nucleic acids. The term "nucleic acid" used herein means and includes double-stranded, single-stranded, partially double-stranded or partially single-stranded DNAs or RNAs.

The process for promoting the release of nucleic acids from a nucleic acid-bearing material in step 1 according to the invention includes mechanical processes using mortars, ultrasound or microwaves or the like, chemical processes using surfactant, denaturants or the like, biochemical processes, and combinations of these processes.

As examples of the accelerator substance for the binding of nucleic acids to a solid phase, there may be mentioned NaI (sodium iodide), KI (potassium iodide), $NaClO_4$, NaSCN (sodium thiocyanate), GuSCN (guanidine thiocyanate) and other chaotropic agents. These substances, however, have a lower end of the peak absorbance at around 260 nm, at which nucleic acids have the peaks. Therefore, if any of these substances contaminates the purified nucleic acid solution, it can adversely affect the assay results of purity or quantity of the nucleic acids with the use of a spectrophotometer, whereas such a spectrophotometer is generally employed in the assays.

Further, NaSCN and GuSCN each containing thiocyanic acid produce lethal HCN (hydrogen cyanide) by a reaction with an acid, waste containing these substances should be treated with care.

Accordingly, GuHCl (guanidine hydrochloride) should preferably be used as the accelerator substance in the present invention. GuHCl is easily available and invites a remarkably lower adverse effect on the absorbance at 260 nm than the other chaotropic agents. In addition, it has no potential risk of producing a lethal gas.

The final concentration of GuHCl in the invention should advantageously fall in the range from 4 to 6 mol/liter for the specific binding of nucleic acids to a solid phase.

As the solid phase bondable to nucleic acids used in step 3 according to the invention, any silicon dioxide-containing substance can be employed, including glass beads, silica powder, quartz filter paper, quartz wool or crushed products of these substances, and diatomaceous earth. Preferably, the use of particles having a small particle size is advantageous for enhancing the contact probability between nucleic acids and the solid phase in the mixture of nucleic acids and a chaotropic agent, and hence for enhancing the binding efficiency or shortening the binding time thereof.

The particle size of the solid phase used in the present invention should preferably fall in the range from about 1 to about 100 $\mu$m. In addition, a suitable stirring operation according to the specific gravity of the particles is desirable for enhancing the contact probability between nucleic acids and the solid phase.

The isolation of the solid phase from a liquid in step 4 according to the invention can be conducted by centrifugation or filtration. When the isolation step is automatized or mechanized, any of known B/F (bond form/free form) isolation techniques generally used in immunoassay devices utilizing antigen-antibody reactions can be employed.

Step 5 for washing the nucleic acid-binding solid-phase with a solution containing a salt can be carried out by mixing the solid phase after completion of step 4 with a salt-containing solution while maintaining the binding of nucleic acids to the solid phase, and isolating the solid phase from a liquid in a similar manner as step 4.

Step 5 can be divided into step 5a for removing non-nucleic-acid components being non-specifically bound to the solid phase from the solid phase, and step 5b for removing the accelerator substance from the solid phase by washing. The liquid used in step 5a or step 5b for washing the solid phase should be one which does not elute the binding nucleic acids from the solid phase, as such property of the liquid affects the final yield of nucleic acids.

Whereas ethanol solution having a concentration of 75% or more is not employed as the washing solution in the invention, GuHCl is preferably used as the solution in step 5a as in step 4. GuHCl has a denaturing activity, and the use of this substance in a concentration ranging from 4 to 6 mol/liter can remove non-specifically absorbed substances from the solid phase.

As the washing solution used in step 5b, those containing a salt which does not adversely affect the eluted nucleic acids and is capable of preparing an aqueous solution at a midrange concentration are desirable. This utilizes the nature that non-dissolved nucleic acids on the surface of the solid phase are insoluble in an aqueous solution containing a high concentration of a salt. By way of illustration, an aqueous solution of KOAc (potassium acetate) at a concentration of 500 mM or more is preferably employed. A mixture of an aqueous solution containing a salt and an alcohol can also be used in step 5b.

In the above case, the concentration of salt in the mixture can be reduced as compared with a single use of the salt, and such a mixture is permissive about the variation of alcohol concentration due to volatilization of the alcohol component. The use of a 50% ethanol aqueous solution containing 50 mmol/liter or more of NaCl is advantageous in the invention.

When an alcohol-containing solution is used in step 5b, addition of step 7 after step 6 is required for removing a trace alcohol component which may possibly contaminate the solution of purified nucleic acids. Step 7 can be conducted by heating the solution, for instance.

Step 6 for eluting nucleic acids from the solid phase can be carried out by mixing the solid phase after washing with an equivalent volume or more of aqueous salt solution of a low concentration, or water. The nucleic acids migrate from the solid phase to an aqueous phase by this operation, and an aqueous solution of purified nucleic acids can be obtained by isolating the solid phase from the liquid in a similar manner to step 4.

The aqueous salt solution of a low concentration or water used in the invention should preferably be sterilized, or be treated with DEPC (diethylpyrocarbonate) as necessary.

The aqueous salt solution of a low concentration or water in this step should preferably be used at a temperature of 55 to 60° C. for enhancing the yield of nucleic acids, or similar advantages can be obtained when the container used for elution is heated at a similar temperature to the above.

For enhancing the yield of nucleic acids, step 6 is preferably conducted at least twice.

The washing procedure in step 5 is carried out using a washing solution containing an acetate or chloride. Examples of the washing solution include an aqueous solution containing 0.5 mol/liter or more of potassium acetate and an aqueous solution containing 0.2 mol/liter of potassium chloride.

The washing solution used in step 5b can be a solution containing 40% of ethanol and 10 mmol/liter or more of potassium acetate, or a solution containing 40% of ethanol and 25 mmol/liter or more of sodium chloride.

The solid phase bondable to nucleic acids used in step 3 may be substances containing silicon dioxide.

The present invention as constructed above has the following advantages.

The invention can provide methods and apparatus for the recovery of nucleic acids, by which nucleic acids having a high purity can be rapidly and easily recovered from a material containing nucleic acids without deteriorating the yield, as compared with processes using washing steps with a single use of sodium chloride solution.

In other words, nucleic acids at a suitable purity for genetic tests or gene analyses can be rapidly and easily recovered without the use of hazardous substances.

In addition, methods and apparatus for the recovery of nucleic acids which are suitable for apparatus for the automatic recovery of nucleic acids from a biological sample can be provided.

Further, methods and apparatus for the recovery of nucleic acids, which are suitable for apparatus for automatically recovering plasmid DNAs from *E. coli,* can be obtained.

Embodiment 8

Recovery of added RNAs

Figure 12:
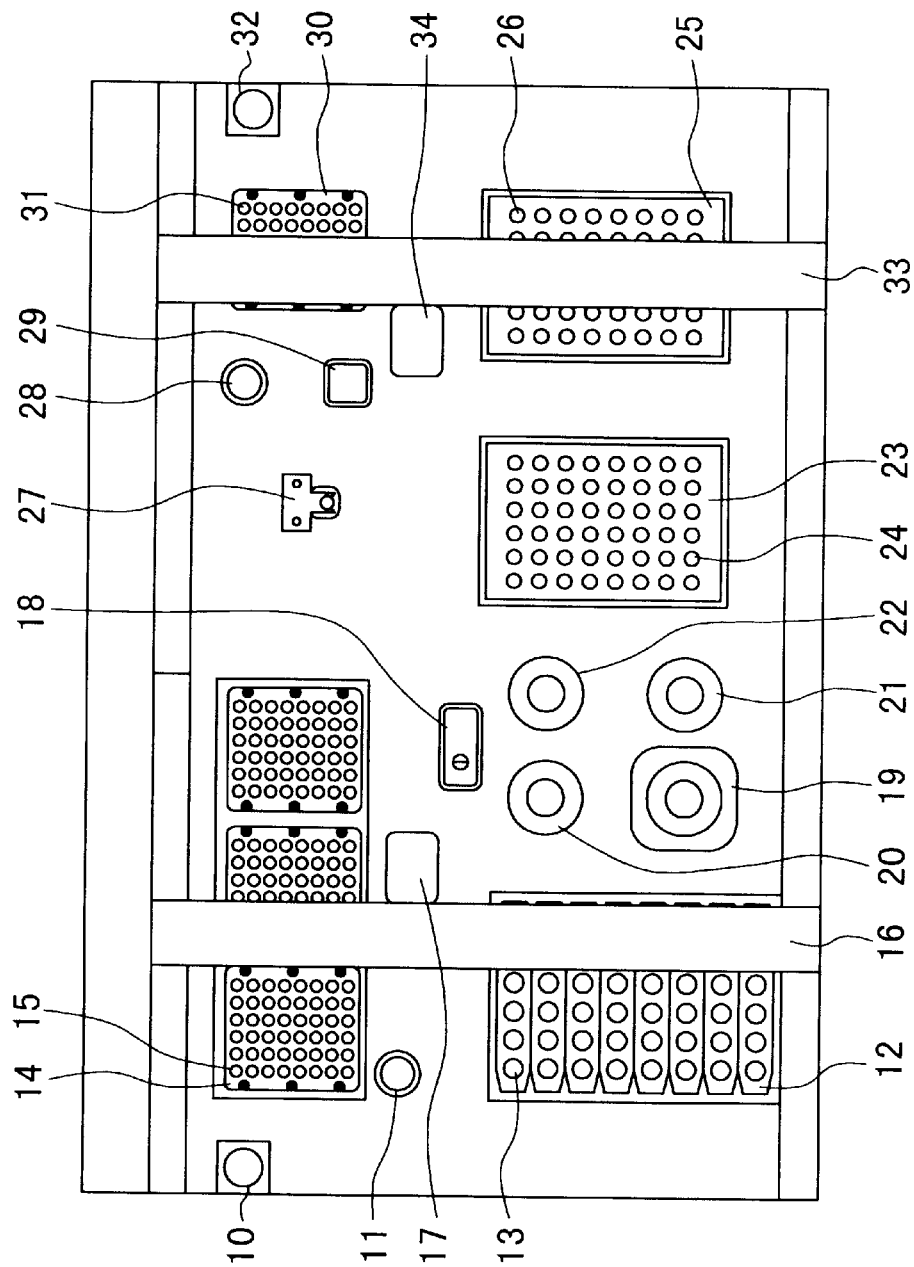
FIG. 12 is a generally plan view of an apparatus for the recovery of nucleic acids according to the eighth embodiment of the invention.
Figure 13:
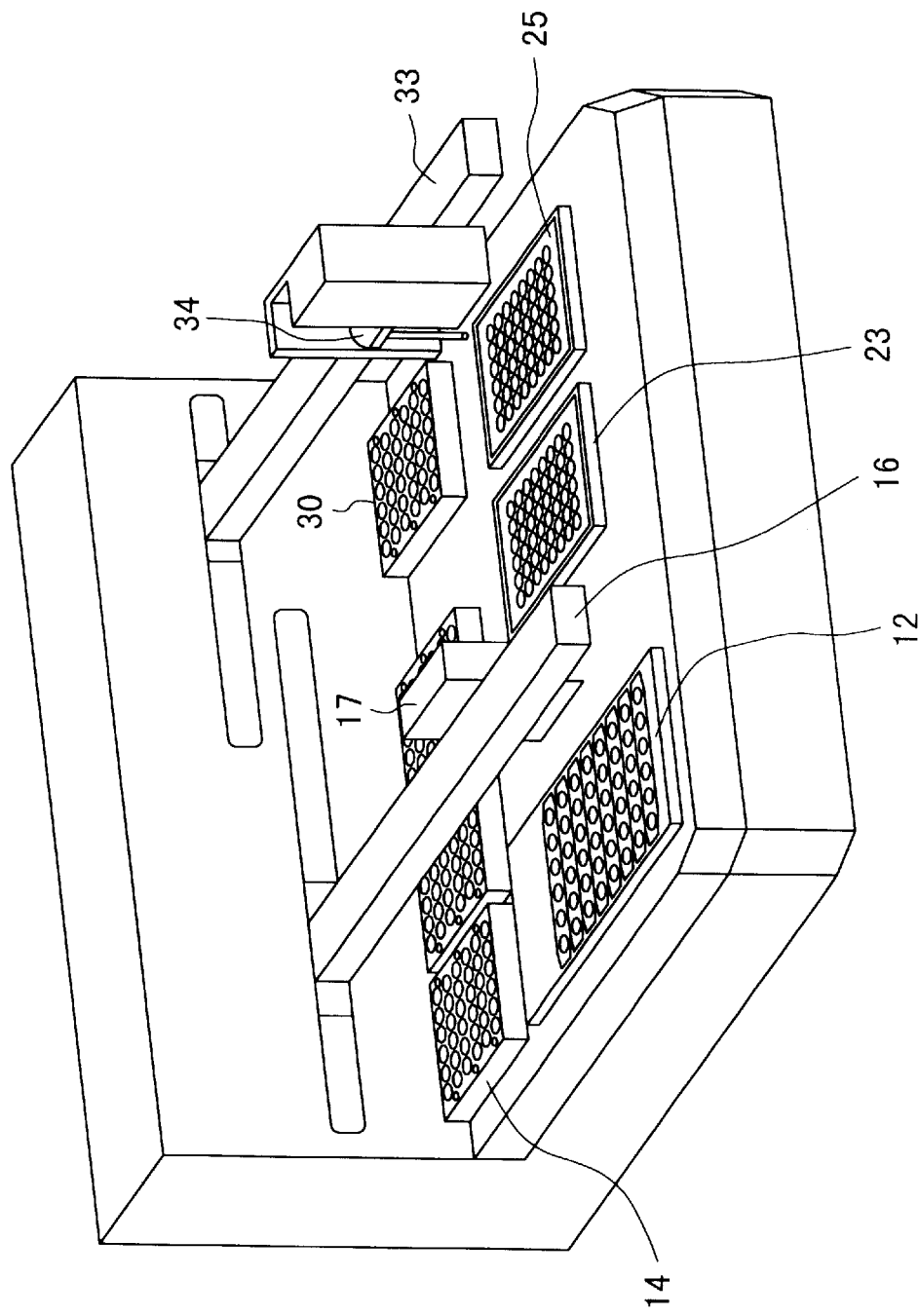
FIG. 13 is a generally perspective view of the apparatus shown in FIG. 12.
Figure 14:
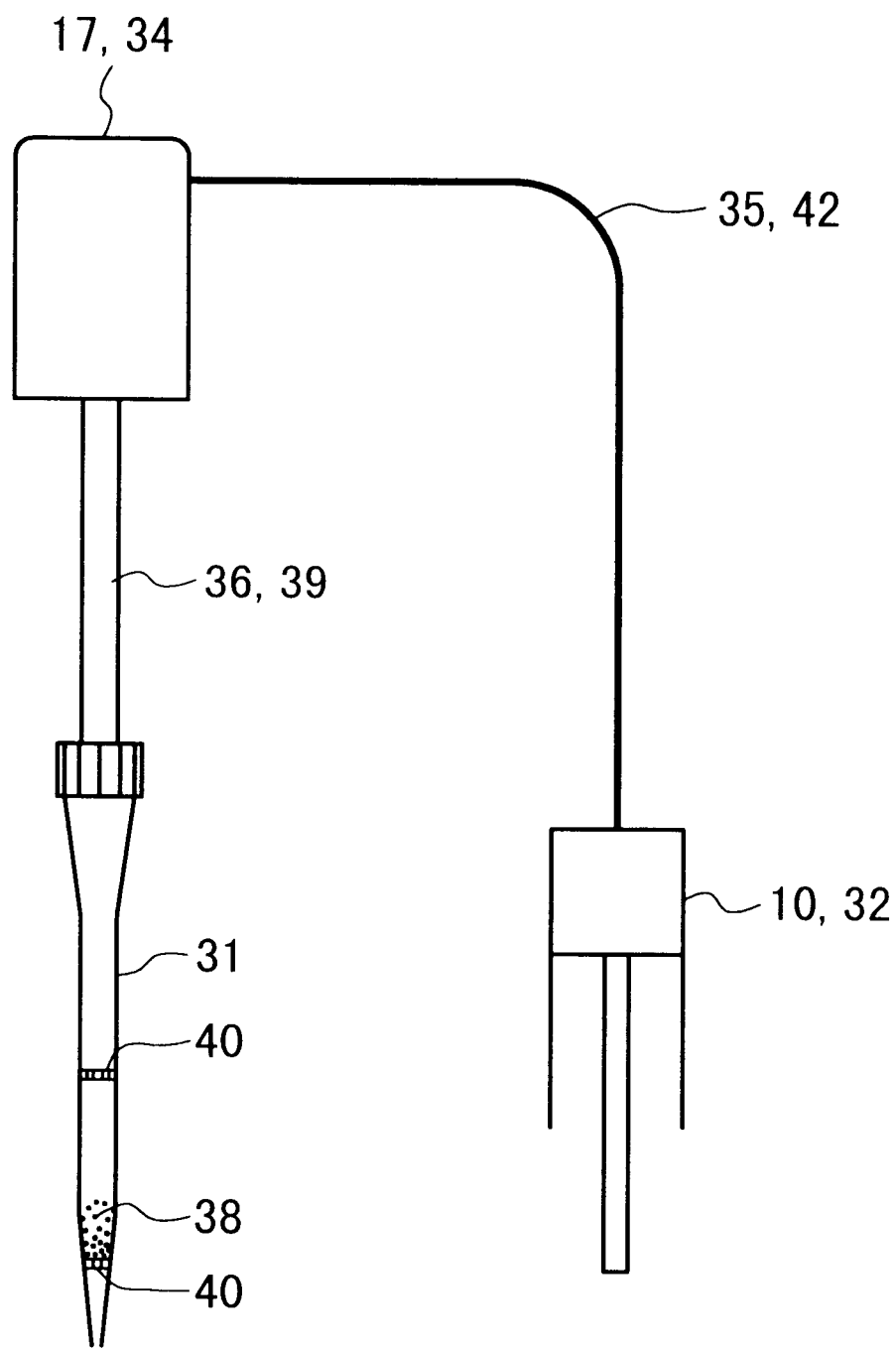
FIG. 14 is a view of a flow path for recovering a nucleic acid by passage through a nozzle holder and a nozzle from a syringe.
Figure 15:
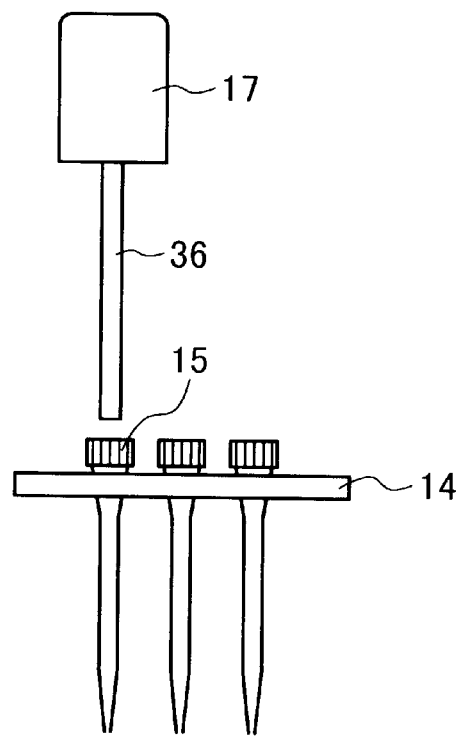
FIG. 15 is a view explanatory of the manner in which distributing chips are engaged with the nozzle.

FIG. 12 is a generally plan view illustrating an apparatus for the recovery of nucleic acids for use in implementing the method for the recovery of a nucleic acid component having specific sequence, which constitutes one embodiment of the present invention. FIG. 13 is a generally perspective view of the apparatus shown in FIG. 12. FIG. 14 is a view showing a flow path for recovering a nucleic acid by passage through a nozzle holder and a nozzle from a syringe. FIG. 15 is a view explanatory of the manner in which distributing chips are engaged with the nozzle, and FIG. 16 a view explanatory of the manner in which a distributing chip is disengaged from the nozzle.

In FIG. 12 through FIG. 16, syringes 10 and 32 are disposed to individually automatically control suctioning and discharging of solutions. The syringes 10 and 32 are individually connected via pipes 42 and 35 to nozzles 36 and 39.

The nozzles 36 and 39 are fixed to nozzle holders 17 and 34. Both of the nozzle holders are connected respectively to arms 16 and 33 such that they are movable in their respective Y and Z directions.

The arms 16 and 33 are individually positioned to be movable in an X direction so that they can be held in partially overlapped relation to each other in the X direction with a positional difference set axially in the Z direction. The nozzle holders 17 and 34 and the arms 16 and 33 can be prevented, due cooperative movement of both members, from displacement toward main portions of the apparatus when seen in plane.

Here, the Y direction denotes upper and lower directions in FIG. 12, the X direction denotes left and right directions in FIG. 12, and the Z direction denotes front and back sides of a drawing sheet of FIG. 12.

A distributing chip holder 14 is sized to receive distributing chips 15 therein, namely 3 distributing chips of the same size. A rack 23 of reaction containers 24 is dimensioned to accommodate 48 reaction containers. Disposed downwardly of a rack of purified products 25 is an insulating mechanism (not shown) to maintain cold the purified products 25.

A washing solution bottle 19, an eluting solution bottle 20, a diluting solution bottom 21 and a bonding accelerator bottle 22, each one by one, are arranged above the nucleic acid-recovering apparatus. Heating mechanisms (not shown) are located downstream of the eluting solution bottom 20 and the bonding accelerator bottle 22 such that both of the bottles are heated from the bottom. Also disposed is a rack 30 of separating chips 31 (pipe-like chips) in which they can be placed in the number of 48.

In FIG. 15, the arm 16 and the nozzle holder 17 are so controlled as to be moved such that the nozzle 36 is positioned with the arm 16 controlled against movement above the distributing chip 15 on the chip holder 14. Subsequently, the nozzle holder 17 is moved downwardly of the nozzle 36 so that the distributing chip 15 is put in place in contact with the nozzle 36. In this way, the distributing chip 15 can be secured automatically to the nozzle 36 at its tip.

Similar controlling is performed with the respect to the nozzle 39, the nozzle holder 34 and the arm 33. Thus, the distributing chip 31 is secured to the nozzle 39 at its tip.

Figure 16:
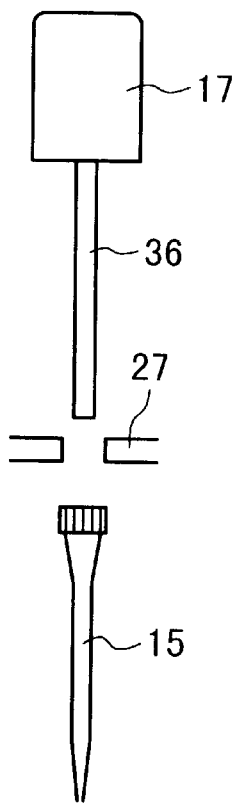
FIG. 16 is a view explanatory of the manner in which a distributing chip is disengaged from the nozzle.

In FIG. 16, the arm 16 and the nozzle holder 17 are then manipulated to move the nozzle 36 upwardly forwardly of a chip puller 27. Thereafter, the nozzle holder 17 is so moved that a joint between the nozzle 36 and the distributing chip 15 is located downwardly of the chip puller 27, and the nozzle 36 is also moved toward the chip puller 27.

Subsequently, the nozzle 17 is moved upwardly while a part of the nozzle 36 is being held in contact with the chip puller 27. In this way, the distributing chip 15 can be disengaged automatically from the nozzle 36.

Similar controlling is performed with the respect to the nozzle 39, the nozzle holder 34 and the arm 33. Thus, the distributing chip 31 is disengaged from the nozzle 39.

A plurality of chip pullers 27 may be arranged to match the kinds of chips used. This allows waste chips to be collected separately.

Solution reservoirs 11 and 28 accommodate solutions discharged from the nozzles 36 and 39, thus serving as home positions and transporting the reserved solutions. On a washing table 18, the distributing chip 15 attached by the nozzle 36 to the nozzle holder 17 is washed by causing running water to be discharged.

In FIG. 14, the separating chips 31 has holding members 40 and 40 disposed at upper and lower portions thereof, and a solid phase 38 is encapsulated and maintained in the separating chip 31 by the holding members 40 and 40. Namely, the solid phase is restricted not so as to displace into the nozzles 36 and 39 (pipes) from the separating chip 31. The bore diameter of the holding member 40 is made smaller than the outer diameter of the solid phase.

The inner diameter of the separating chip 31 is divergent toward its tip, whereas the outer diameter of the solid phase 38 is larger than the inner diameter of the tip of the separating chip 31. Consequently, the solid phase can be prevented from getting discharged from the tip of the separating chip 31.

Protrusions are disposed on an inner wall of the separating chip 31, which protrusions act as guides in positioning the holding members 40 in the separating chip 31.

The separating chip 31 can be accommodated in a rack 30 of separating chips located on the apparatus of FIG. 12.

As a specimen, there was used a solution of mRNA (messenger RNA) obtained in commerce and prepared to have a selected concentration with the use of TE (10 mM Tris, 1 m MEDTA buffer solution). The specimen was placed in a rack 12 located on the apparatus of FIG. 12.

A separating chip rack 14 in which the separating chip 15 had been received, a separating chip rack 14 in which the separating chip 31 had been received, reagent bottles, a reactor 24 and a pure product collector 26 were set on the nucleic acid-recovering apparatus shown in FIG. 12, followed by manipulation of the apparatus as predetermined.

Here, the separating chip 31 was produced by forming the holding member 40 from a hydrophilic polyvinylidene fluoride resin, by positioning the holding member at near to the tip of the separating chip 31, by adding thereto the solid phase in a constant amount and further by pressing the holding member 40 therein.

To recover a nucleic acid of poly (A) sequence, use was made as the solid phase 38 a commercially available oligo (dT) cellulose equilibrated in the presence of a binding accelerator. Substances other than one used here may be used insofar as they have specific base sequence, and they may be formed by any suitable conventional technique according to the sort of sequences to be recovered.

In the washing solution bottle 19, a washing solution was placed which had been prepared from pure water derived from DEPC treatment of an aqueous solution containing 100 mM of NaCl, 10 mM of Tris-HCl (pH 7.5) and 1 mM of EDTA.

In the eluting solution bottle 20, an eluting solution was placed which had been prepared from pure water derived from DEPC treatment of an aqueous solution containing 10 mM of Tris-HCl (pH 7.5) and 1 mM of EDTA.

In the bonding accelerator bottle 22, a bonding accelerator was placed which had been prepared from pure water derived from DEPC treatment of an aqueous solution containing 600 mM of NaCl, 10 mM of Tris-HCl (pH 7.5), 1 mM of EDTA and 0.1% of SDS.

The recovery of a nucleic acid will now be described as one embodiment of the present invention.

In a first step, the arm 16 and nozzle holder 17 are manipulated to move, thereby securing the distributing chip 15 to the nozzle 36 as predetermined. By subsequent manipulation of the arm 16, the nozzle holder 17 and the syringe 10, the bonding accelerator is suctioned in a selected amount from the bonding accelerator bottle 22. After being incorporated by suction with a selected amount of air, the nozzle 36 is moved toward the washing table 18 where the distributing chip 15 was washed on its outer wall with running water.

Upon completion of the washing, the nozzle holder is moved toward a selected specimen 13 on the specimen rack 12, and a selected amount of the specimen is suctioned into the nozzle 36 by the movement of the syringe 10. After suction of the specimen, the nozzle holder 17 is manipulated to move to a selected reactor 24 on the reactor rack 23, and the specimen contained in the nozzle 36 is discharged in the total amount.

Subsequently to discharging of the specimen, the nozzle 36 is further subjected to suction and discharging of the specimen so that the specimen and the bonding accelerator are mixed with each other. Then, the nozzle holder 17 is moved by controlled manipulation to the chip puller 27 by which the distributing chip 15 is disengaged from nozzle 36 as predetermined.

In a second step, the arm 33 and the nozzle holder 34 are manipulated to secure the separating chip 31 to the nozzle 39 and then to move the nozzle holder 34 to the reactor 24 on the reactor rack 23 in which the aforementioned mixed solution has been accommodated. By control of the syringe 32, the mixed solution is suctioned into the separating chip 31. After completion of the suction, the nozzle 39 is caused by control of the syringe 32 to repeat suction and discharging in a selected number of cycles so that the solid phase 38 bondable to specific base sequence is brought into contact with the mixed solution.

In a third step, after repetition of suction and discharging by the nozzle 39 in a selected number of cycles and after suction of the mixed solution of the reactor 24 in the separating chip 31, the nozzle 39 is moved by control of the arm 33 and the nozzle holder 34 to the waste Outlet 29 where the mixed solution contained in the separating chip 31 is discharged by control of the syringe 32. The nozzle 39 is then moved to the solution reservoir 28 by control of the arm 33 and the nozzle holder 34.

In a fourth step, the distributing chip 15 is secured to the nozzle 36 by controlled manipulation of the arm 16 and the nozzle holder 17, and a selected amount of the washing solution is suctioned from the washing solution bottle 19 by control of the arm 16, the nozzle holder 17 and the syringe 10. The nozzle holder 17 is moved to a selected reactor 24 on the reactor rack 23, and the washing solution is then discharged in the reactor 24 from the nozzle 36.

After the discharging, with the arm 16 and the nozzle holder 17 controlled, the nozzle holder 17 is moved to the chip puller 27 where the distributing chip 15 is disengaged from the nozzle 36 as predetermined.

Upon movement of the nozzle holder 17, the nozzle 36 is moved by control of the arm 33 and the nozzle holder 34 to a selected reactor 24 on the reactor rack 23 in which the washing solution has been contained. The washing solution is suctioned in the separating chip 31 by control of the syringe 32. Suction and discharging are then repeated in a selected number of cycles with the syringe 32 controlled so that the solid phase 38 is washed with the washing solution.

After repetition of suction and discharging by the nozzle 36 in a selected number of cycles and after suction of the mixed solution of the reactor 24 in the separating chip 31, the nozzle 36 is moved by control of the arm 33 and the nozzle holder 34 to the waste outlet 29 where the mixed solution contained in the separating chip 31 is discharged by control of the syringe 32. The nozzle 36 is then moved to the solution reservoir 28 by control of the arm 33 and the nozzle holder 34.

The fourth step may be repeated, when desired, in a selected number of cycles. In this instance, this step may be repeated as it is, or the washing solution may be suctioned in the distributing chip 15 in a plurality of batches so that a desired amount of the washing solution is discharged in the reactor 24. After the discharging, the nozzle 36 is moved to the solution reservoir 11 where the separating chip 31 is manipulated as predetermined, and a desired amount of the washing solution is again discharged in the reactor 24. Thus, the fourth step can be repeated with high efficiency.

In a fifth step, with the arm 16 and the nozzle holder 17 controlled, the distributing chip 15 is secured to the nozzle 36 as predetermined. By control of the arm 16, the nozzle holder 17 and the syringe 10, a selected amount of the eluting solution is suctioned from the eluting solution bottle 20. The nozzle holder 17 is moved by controlled manipulation on to the reactor rack 23 where the washing solution contained in the nozzle 36 is discharged in a selected reactor 24.

After the discharging, with the arm 16 and the nozzle holder 17 controlled, the nozzle holder 17 is moved to the chip puller 27 where the distributing chip 15 is disengaged from the nozzle 36 as predetermined.

Upon movement of the nozzle holder 17, the nozzle 36 is moved by control of the arm 33 and the nozzle holder 34 to a selected reactor 24 on the reactor rack 23 in which the eluting solution has been contained. The eluting solution is suctioned in the separating chip 31 by control of the syringe 32. Suction and discharging are then repeated in a selected number of cycles with the syringe 32 controlled so that the solid phase 38 is contacted with the eluting solution.

After repetition of suction and discharging by the nozzle 36 in a selected number of cycles and after suction of the eluting solution of the reactor 24 in the separating chip 31, the nozzle 36 is moved by control of the arm 33 and the nozzle holder 34 to the pure product collector 26 where the eluting solution contained in the separating chip 31 is discharged by control of the syringe 32. The nozzle 36 is then moved to the solution reservoir 28 by control of the arm 33 and the nozzle holder 34.

The fifth step may be repeated, when desired, in a selected number of cycles. In this instance, this step may be repeated as it is, or the eluting solution may be suctioned in the distributing chip 15 in a plurality of batches so that a desired amount of the eluting solution discharged in the reactor 24. After the discharging, the nozzle 36 is moved to the solution reservoir 11 where the separating chip 31 is manipulated as predetermined, and a desired amount of the eluting solution is again discharged in the reactor 24. Thus, the fourth step can be repeated with high efficiency.

Upon completion of the fifth step, with the arm 33 and the nozzle holder 34 controlled, the nozzle holder 34 is moved to the chip puller 27 where the separating chip 31 is disengaged from the nozzle 39 as predetermined.

A sixth step is directed to a step for low temperature-insulating, with the use of a low-temperature insulator, an eluate obtained in the fifth step and containing a nucleic acid component of specific sequence.

As a test specimen, there was used a part of the eluate received in the pure product collector 26 after the fourth step and the fifth steps among the above steps had been repeated twice, respectively. The amount of the nucleic acid thus recovered was determined from an absorbance at 260 nm, and the ratio of recovery was calculated on the basis of the amount of the nucleic acid prior to treatment. This ratio proved to be 72%. The time required for one specimen to be treated was found to be in the order of 10 minutes.

Additionally, a part of the recovered nucleic acid was used for PCR treatment of a reverse-transfer protease induced from AMV (Avian Myeloblastosis Virus, or derived by addition of reagents for reverse transfer, by heating the mixture and by reverse-reacting the mixture. It has been found that cDNA is amplified.

From the above results and according to the present invention, a nucleic acid is recoverable with utmost simplicity and high recovery.

As stated hereinabove, one embodiment of the present invention provides a method for and an apparatus for the recovery of nucleic acids which enable a nucleic acid to be speedily simply recovered from nucleic acid-containing materials with high purity and low cost and which enable a nucleic acid component of specific sequence to be automatically recovered from biological specimens containing such component.

The present invention is suitably applicable to nucleic acid-containing materials, particularly to clinical specimens such as of live blood, blood serum, phlegm, urine and the like, or biological specimens such as of cultured cells, cultured bacteria and the like.

The method of the present invention is also useful for reaction products such as of amplified protease of DNA and the like, and coarsely pure nucleic acid-containing materials. By the nucleic acid noted herein is meant DNA (desoxyribonucleic acid) or RNA (ribonucleic acid) which is of a double- or single-chained structure, or of a partly double- or single-chained structure.

In the first step according to the present invention, suitable substances for use in accelerating bonding of a nucleic acid to a solid phase are sodium chloride (NaCl), lithium chloride (LiCl) and the like.

Other substances may be used in case they do not adversely affect treatments after a nucleic acid is recovered, but can promote bonding of a nucleic acid to a solid phase.

When needed, heating means may be disposed. Desirably, heating is performed at about 65° C. by the use of such means after a solid phase and a binding accelerator are mixed together. Similar good results can be produced even when a binding accelerator used is heated at that temperature, or when a heater of desired temperatures is arranged around a position where a solid phase is placed.

The solid phase useful in the second step according to the present invention is a substance which is bondable to a specific base sequence and which is retentive of a nucleic acid in the second step to the fourth step and is insoluble in the first step to the fourth step. To preclude the solid phase from becoming escaped from a chip, the tip of the solid phase has an inner diameter of smaller than that of the joint where the chip is connected to the corresponding pipeline, and the outer diameter of the solid phase is larger than the inner diameter of the tip of the chip.

Alternatively, a holding member may be disposed inwardly of and adjacent to the tip of the chip, which holding member has a smaller bore diameter than the outer diameter of the solid phase. A solid phase may be sintered such that it is capable of insertion in the chip and of passage of a solution therethrough. An inner wall of the chip may be used as a solid phase. To this end, conventional forming techniques can be utilized. Desirably, the holding member has as large a bore as possible but to an extent to prevent a solid phase from runway.

Improved bonding efficiency and shortened working time are attainable by enhanced probability of contact between a nucleic acid and a solid phase in a mixed solution of a nucleic acid and a bonding accelerator. It is desired, therefore, that suction and discharging of a solution be performed between a chip and a container in a plurality of batches by means of a distributing mechanism.

The non-bondable component in the third step according to the present invention is separated by discharging a solution component from a pipeline by means of a distributing mechanism.

Washing of a solid phase in the fourth step according to the present invention is conducive to improved bonding efficiency and shortened working time. Preferably, therefore, suction and discharging of a solution are effected between a chip and a container in a plurality of batches by means of a distributing mechanism.

A washing solution used in this instance is preferably one which can maintain bonding of a nucleic acid to a solid phase obtained in the second step, while washing out undesirable components.

Elution of a nucleic acid from a solid phase in the fifth step according to the present invention is attained by mixing an aqueous solution having sodium chloride contained at a low concentration with respect to a solid phase of the fourth step. Thus, since the nucleic acid is migrated from a solid phase to an aqueous one, a pure nucleic acid solution is obtained by discharging the solution from the pipeline by means of a distributing mechanism as is in the third step.

The aqueous solution of a low sodium chloride content used in the present invention is preferably sterilized or treated where needed with DEPC (diethyl pyrocarbonate).

The aqueous solution of a low sodium chloride content employed herein is preferably used after being heated at about 65° C. in order to enhance the yield of a nucleic acid to be recovered. Similar good results can be produced even when a binding accelerator used is heated at that temperature, or when a heater of desired temperatures is arranged around a position where a solid phase is placed.

To enhance the yield of a nucleic acid to be recovered, suction and discharging of a solution are effected between a chip and a container and in a plurality of batches, followed by discharging of the solution in its total amount. More preferably, the fifth step is repeated at least twice.

Insulation of an eluate effected in the sixth step according to the present invention is attained by cooling the solution obtained after the fifth step has been completed. This step permits the recovered nucleic acid to be held stable.

Furthermore, according to the present invention, a nucleic acid having a poly (A) sequence can be recovered by causing part of a solid phase 38 to be formed from oligonucleotide having a repeating unit of deoxythymidilic acid.

According to the present invention, there is provided a method for and an apparatus for the recovery of nucleic acids which are speedy, simple and inexpensive to recover highly pure nucleic acids from nucleic acid-containing materials and which are capable of automatically recovering nucleic acid components of specific sequences present in biological specimens.

Other embodiments and variations will be obvious to those skilled in this art; this invention is not to be limited except as set forth in the following claims.

What is claimed is:

1. An apparatus for recovering nucleic acids from a nucleic acid bearing material, which comprises:
   a) a reactor to receive a sample, a reagent, a washing solution and an adsorbing solid phase, and a reactor transport mechanism to carry the reactor to predetermined positions;
   b) at least one pipette to provide a given volume of a reagent, accelerator and/or a washing solution to the sample in the reactor;
   c) motors to control said at least one pipette and the reactor transport mechanism;
   d) a mechanical control unit to control the motors;
   e) a computer that controls the mechanical control unit; and f) a purified product container,
   wherein the mechanical control unit controls the apparatus such that the following steps are conducted in order;
   a first step of releasing nucleic acids from the nucleic acid bearing material in the reactor and containing the released nucleic acids in the reactor,
   a second step of mixing the released nucleic acids with an accelerator using said at least one pipette to form a mixture for binding the nucleic acids to the adsorbing solid phase in the reactor, and
   a third step of contacting the adsorbing solid phase in the reactor with the mixture from the second step using said at least one pipette to bind the nucleic acids to the solid phase.

2. The apparatus according to claim 1, further including a magnet adjacent the reactor transport mechanism, wherein magnetic particles are said adsorbing solid phase and the mechanical control unit controls the apparatus such that after the third step the following steps are conducted in order, a fourth step of isolating the adsorbing solid phase containing bound nucleic acids from a solution in the reactor with said magnet, a fifth step of washing the nucleic acids bound to the solid phase with an aqueous solution containing alcohol and a salt, a sixth step of eluting the nucleic acids from the solid phase to obtain purified nucleic acids, and a seventh step of recovering the purified nucleic acids in the purified product container.

3. An apparatus for recovering nucleic acids from a nucleic acid bearing material, comprising:
   a) a reactor to receive a sample, a reagent, a washing solution and an adsorbing solid phase;
   b) at least one pipette to provide a given volume of a reagent, accelerator and/or a washing solution to the sample in the reactor;
   c) a purified product container;
   d) a reactor transport mechanism to carry the reactor to predetermined positions;
   e) a purified product transport mechanism to carry the purified product container to predetermined positions;
   f) motors to control said at least one pipette, the reactor transport mechanism and the purified product transport mechanism
   g) a mechanical control unit to control the motors; and
   h) a computer that controls the mechanical control unit, wherein the mechanical control unit controls the apparatus such that the following steps are conducted in order;
   a first step of releasing nucleic acids from the nucleic acid bearing material in the reactor and containing the released nucleic acids in the reactor,
   a second step of mixing the released nucleic acids with an accelerator using said at least one pipette to form a mixture for binding the nucleic acids to an adsorbing solid phase in the reactor, and
   a third step of contacting the adsorbing solid phase in the reactor with the mixture from the second step using said at least one pipette to bind the nucleic acids to the solid phase.

4. The apparatus according to claim 3, further including a magnet adjacent the reactor transport mechanism, wherein magnetic particles are as said adsorbing solid phase and the mechanical control unit controls the apparatus such that after the third step 2, a fourth step of isolating the adsorbing solid phase containing sound nucleic acids from a solution in the reactor using the magnet, a fifth step of washing the nucleic acids bound to the solid phase with an aqueous solution containing alcohol and a salt using said at least one pipette, and a sixth step of eluting the nucleic acids from the solid phase to obtain purified nucleic acids.

5. The apparatus according to claim 4, wherein the mechanical control unit controls the apparatus such that after the sixth step the following step is conducted, a seventh step of recovering the purified nucleic acids in the purified product container using said at least one pipette.

6. The apparatus according to claim 3, further including a magnet adjacent the reactor transport mechanism, wherein magnetic particles are said adsorbing solid phase and the mechanical control unit controls the apparatus such that after the third step the following steps are conducted in order, a fourth step of isolating the adsorbing solid phase containing bound nucleic acids from a solution in the reactor with the magnet, a fifth step of washing the nucleic acids bound to the solid phase with an aqueous solution containing alcohol and a salt to remove non-nucleic acid components using said at least one pipette, and a sixth step of washing the nucleic acids bound to the solid phase with an aqueous solution containing alcohol and a salt to remove the accelerator from the nucleic acids using said at least one pipette to obtain purified nucleic acids.

7. The apparatus according to claim 6, wherein the mechanical control unit controls the apparatus such that after the sixth step the following step is conducted, a seventh step of recovering the purified nucleic acids in the purified product container using said at least one pipette.

* * * * *